United States Patent
Malisauskas et al.

(10) Patent No.: US 11,921,117 B2
(45) Date of Patent: Mar. 5, 2024

(54) CHARACTERIZATION OF SUBVISIBLE PARTICLES USING A PARTICLE ANALYZER

(71) Applicants: Baxalta Incorporated, Bannockburn, IL (US); Baxalta GmbH, Zug (CH)

(72) Inventors: Mantas Malisauskas, Vienna (AT); Christian Lubich, Vienna (AT); Thomas Prenninger, Vienna (AT); Birgit Reipert, Deutsch Wagram (AT)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 1395 days.

(21) Appl. No.: 16/298,520

(22) Filed: Mar. 11, 2019

(65) Prior Publication Data

US 2019/0271706 A1    Sep. 5, 2019

Related U.S. Application Data

(63) Continuation of application No. 13/739,812, filed on Jan. 11, 2013, now Pat. No. 10,274,500.

(60) Provisional application No. 61/747,720, filed on Dec. 31, 2012, provisional application No. 61/585,425, filed on Jan. 11, 2012.

(51) Int. Cl.
| | |
|---|---|
| *G01N 33/68* | (2006.01) |
| *C12Q 1/56* | (2006.01) |
| *G01N 15/10* | (2006.01) |
| *G01N 15/14* | (2006.01) |
| *G01N 33/487* | (2006.01) |
| *G01N 33/86* | (2006.01) |

(52) U.S. Cl.
CPC ........... *G01N 33/6839* (2013.01); *C12Q 1/56* (2013.01); *G01N 15/1012* (2013.01); *G01N 15/1429* (2013.01); *G01N 33/48735* (2013.01); *G01N 33/6803* (2013.01); *G01N 33/86* (2013.01); *G01N 2015/1493* (2013.01)

(58) Field of Classification Search
CPC ........... G01N 33/6839; G01N 15/1012; G01N 15/1429; G01N 33/48735; G01N 33/6803; G01N 2015/1493; C12Q 1/56
See application file for complete search history.

(56) References Cited

U.S. PATENT DOCUMENTS

| | | | |
|---|---|---|---|
| 4,704,891 A | 11/1987 | Recktenwald et al. | |
| 4,774,339 A | 9/1988 | Haugland | |
| 5,540,494 A | 7/1996 | Purvis, Jr. et al. | |
| 6,423,270 B1 | 7/2002 | Wall | |
| 6,870,165 B2 | 3/2005 | Amirkhanian | |
| 2004/0002110 A1 | 1/2004 | Boga et al. | |
| 2005/0237521 A1* | 10/2005 | Hirono | B01F 25/4331 356/246 |
| 2007/0281360 A1 | 12/2007 | Wolf | |
| 2009/0131640 A1 | 5/2009 | Berkelman | |
| 2009/0311715 A1 | 12/2009 | Owen et al. | |
| 2010/0330368 A1* | 12/2010 | Prud'homme | A61K 49/0093 977/773 |

FOREIGN PATENT DOCUMENTS

| | | |
|---|---|---|
| JP | 2007047154 | 2/2007 |
| JP | 2007505288 | 3/2007 |
| JP | 2007507688 | 3/2007 |
| JP | 2007114026 | 5/2007 |
| JP | 2007533971 | 11/2007 |
| JP | 2009109197 | 5/2009 |
| JP | 2009196916 | 9/2009 |
| WO | 199957566 | 11/1999 |
| WO | 2004015421 | 2/2004 |
| WO | 2013106772 | 7/2013 |

OTHER PUBLICATIONS

Oct. 4, 2016 European Search Report in connection with EP Patent Application No. 13703486.
Mach H. et al., "The use of flow cytometry for the detection of subvisible particles in therapeutic protein formulations." J. Pharm. Sci., vol. 100, No. 5, May 2011, pp. 1671-1678, XP002699698.
Sparrow R.L. et al., "Microparticle content of plasma for transfusion is influenced by the whole blood hold conditions: Pre-analytical considerations for proteomic invenstigations."J. Proteomics, vol. 76, Jul. 2012, pp. 211-219, XP028959196.
Jayachandran M. et al., "Methodology for isolation, identification and characterization of microvesicles in peropheral blood." J. Immun. Meth., vol. 375, No. 1, Oct. 2011, pp. 207-214, XP028434311.
Nilsson K.P.R. et al., (2010) "Structural Typing of Systemic Amyloidoses by Luminescent-Conjugated Polymer Spectroscopy," Am. J. Pathol. vol. 176, No. 2, pp. 563-574.
Office Action dated Dec. 6, 2016 in connection with JP Application No. 2014-552349.
International Search Report for International Application No. PCT/US2013/021313 filed on Jan. 11, 2013.
Palutke et al., Flow cytometric purification of Alzheimer's disease amyloid plaque core protein using thioflavin T. Cytometry 8: 494-499 (1987).
Hawe et al., Extrinsic Fluorescent Dyes as Tools for Protein Characterization, Pharmaceutical Research, 25(7), 2008, 1487-1499.

* cited by examiner

*Primary Examiner* — Changhwa J Cheu
(74) *Attorney, Agent, or Firm* — Troutman Pepper Hamilton Sanders LLP

(57) ABSTRACT

The present specification discloses methods of characterizing a population of particles using a particle analyzer. Particles may be characterized by size, absolute number, whether the particle is non-proteinaceous or proteinaceous, whether a proteinaceous particle has or lacks a certain physical property, or any combination thereof.

19 Claims, 12 Drawing Sheets

CHARACTERIZATION OF SUBVISIBLE PARTICLES USING A PARTICLE ANALYZER

This application is a continuation of U.S. patent application Ser. No. 13/739,812, filed Jan. 11, 2013, which claims priority pursuant to 35 U.S.C. § 119(e) to U.S. Provisional Application 61/747,720 filed on Dec. 31, 2012 and U.S. Provisional Application No. 61/585,425 filed on Jan. 11, 2012, the content of each of which is hereby incorporated by reference in its entirety.

Therapeutic protein products provide unique and effective treatments for numerous human diseases and medical conditions. In many cases, these treatments are used chronically to slow disease progression, reduce morbidity and/or to replace essential proteins that are not produced endogenously in an individual. Factors that reduce or eliminate the effectiveness of a protein-based treatment can lead to patient suffering and even death. One means by which efficacy of therapeutic proteins can be compromised is by an immune response, resulting in antibody-mediated neutralization of the protein's activity or alterations in bioavailability. For example, in the case of treatment of hemophilia A, neutralizing antibodies to Factor VIII can cause life-threatening bleeding episodes, resulting in significant morbidity and necessitating treatment with a prolonged course of a tolerance-inducing therapy to reverse immunity. In other cases, antibodies induced by a exogenous protein-based treatment can cross-react with and neutralize the patient's endogenous protein. If the endogenous protein serves a nonredundant biological function, such an immune response can have devastating results. For example, pure red cell aplasia can result from neutralizing antibodies to epoetin alpha. It has been presupposed that protein aggregates present in a therapeutic protein product may enhance immunogenicity by evoking an immune response. As such, protein aggregates have the potential to negatively impact clinical performance. Therefore, protein aggregates need to be characterized and as part of product characterization and quality assurance programs.

Proteins usually aggregate from partially unfolded molecules, which can be part of the native state ensemble of molecules. Even though product formulations are developed to maximize and maintain the fraction of protein molecules present in the native state, significant amounts of aggregates can form, especially over pharmaceutically relevant time scales and under stress conditions. For example, exposure to interfaces (e.g., air-liquid and solid-liquid), light, temperature fluctuations or minor impurities can induce aggregation. Such exposure can occur during processing steps, as well as in the final product container during storage, shipment and handling. In addition, protein aggregates can be generated from protein alone or from heterogeneous nucleation on foreign micro- and/or nanoparticles that are shed, for example, from filling pumps or product container/closures. Furthermore, the levels and sizes of protein aggregates can be changed by many factors relevant to commercial production of therapeutic proteins. Such factors include a change in the type of filling pump during scale-up to commercial manufacturing, changes in formulation or container/closure, and even unintentional changes in the manufacturing process such as alterations in filling pump mechanical parameters or other unforeseen factors.

Large protein aggregates can be quantified based on the mass percentage for each aggregate size and are usually classified as soluble or insoluble. There is mass balance between the amount of protein in aggregates and the loss of monomeric protein. However, smaller protein aggregates usually do not constitute a sufficient mass fraction of the protein population to be quantified based on aggregate mass or loss of monomeric protein. Typically, these smaller aggregates are quantified by counting the number of particles in given size ranges. As a first approximation, particles are divided into visible particles and subvisible particles. Although no strict size limit can be assigned for when particles become visible to the human eye, it is generally recognized that particles more than 100-200 μm in size are detected with relatively high probability under appropriate testing conditions. Subvisible particles are usually defined as particles that are too large for analysis by size exclusion chromatography (SEC), but too small to be visible to the unaided eye.

Even though protein aggregates are potentially immunogenic, current United States Pharmacopeia (USP) particulate testing is not designed to monitor or assess the presence of protein aggregates in a therapeutic protein product. For example, methods such as nanoparticle tracking analysis (NTA), flow microscopy, electrophoretic light scattering (ELS), light obscuration and electrospray differential mobility analysis (ES-DMA), also known as gas-phase electrophoretic mobility molecular analysis (GEMMA) cannot characterize the detected subvisible particles in terms of their nature (e.g., proteinaceous v. non-proteinaceous), composition, structural properties, chemical properties, amount, and/or size. Thus, there is a need for analytical methods that can assess protein aggregate characteristics. Such methods are important for establishing appropriate quality controls and/or for evaluating and mitigating risk to product quality potentially caused by protein aggregates.

SUMMARY

The present specification provides methods for simultaneous detection, counting and characterization of subvisible particles. Unlike other methods, the presently disclosed methods provide information about the nature (e.g., proteinaceous v. non-proteinaceous), composition, property (e.g., a structural, functional or chemical property), amount, and size of detected subvisible particles. This, in part, is accomplished by the use of a fluorescent dye that detects subvisible particles below 1 μm. This detection can allow for the identification of such subvisible particles from background noise as well as the distinction of proteinaceous subvisible particles from non-proteinaceous subvisible particles and the identification a particular composition or property presence in (or absence from) the proteinaceous subvisible particles. Additionally, the disclosed methods allow for the characterization of individual particles while analyzing a bulk sample.

Thus aspects of the present specification disclose methods of characterizing a population of subvisible particles in a sample using a particle analyzer. In aspects, the method comprises the steps of: a) calibrating a particle analyzer using a size standard; b) interrogating the sample as the sample passes through a sensing zone of the particle analyzer, the sample comprising a fluorescent counting standard and at least one fluorescent dye, wherein the interrogation includes light of one or more wavelengths that can be scattered by the size standard, scattered by or excite the fluorescent counting standard, and scattered by or excite the at least one fluorescent dye, and wherein the at least one fluorescent dye includes a first fluorescent dye that stains a proteinaceous material in a manner that distinguishes the proteinaceous material from a non-proteinaceous material, and a second fluorescent dye that stains a physical property of the proteinaceous material in a manner that distinguishes a proteinaceous material having the physical property from a proteinaceous material not having the physical property; c) collecting data from at least one light scatter parameter and at least one fluorescence parameter, wherein the data collected from the at least one light scatter parameter represents a particle size based upon the size standard calibration, and wherein the data collected from the at least one fluorescence parameter includes a first fluorescence parameter representing presence of the proteinaceous material based upon fluorescence intensity emitted from the first fluorescent dye, a second fluorescence parameter representing a particle number based upon fluorescence intensity emitted from the fluorescent counting standard, and a third fluorescence parameter representing presence of the proteinaceous material having the physical property based upon fluorescence intensity emitted from the second fluorescent dye; and d) analyzing the data to define the particle size, the particle number, presence of the proteinaceous material, and presence of the physical property to determine an absolute number and size of proteinaceous subvisible particles with and without the physical property, thereby characterizing the population of subvisible particles in the sample. In other aspects, an absolute number, size, and presence of a non-proteinaceous material and an absolute number, size, and presence of non-proteinaceous subvisible material with and without a physical property are analyzed in order to characterize the population of subvisible particles in the sample.

Other aspects of the present specification disclose methods of characterizing a population of subvisible particles in a sample using a particle analyzer, the method comprising the steps of: a) calibrating a particle analyzer using a size standard; b) interrogating the sample as the sample passes through a sensing zone of the particle analyzer, the sample comprising a fluorescent counting standard and at least one fluorescent dye, wherein the interrogation includes light of one or more wavelengths that can be scattered by the size standard, scattered by or excite the fluorescent counting standard, and scattered by or excite the at least one fluorescent dye, and wherein the at least one fluorescent dye includes a first fluorescent dye that stains proteinaceous material in a manner that distinguishes a proteinaceous particle from a non-proteinaceous particle; c) collecting data from at least one light scatter parameter and at least one fluorescence parameter, wherein the data collected from the at least one light scatter parameter represents a particle size based upon the size standard calibration, and wherein the data collected from the at least one fluorescence parameter includes a first fluorescence parameter representing presence of a proteinaceous material based upon fluorescence intensity emitted from the first fluorescent dye, and a second fluorescence parameter representing a particle number based upon fluorescence intensity emitted from the fluorescent counting standard; and d) analyzing the data to define the particle size, the particle number, and presence of the proteinaceous material to determine absolute number and size of proteinaceous subvisible particles, thereby characterizing the population of subvisible particles in the sample. The data analysis step may further comprise determining absolute number of sized non-proteinaceous subvisible particles by subtracting the absolute number of all sized subvisible particles by the absolute number of sized proteinaceous subvisible particles. In other aspects, an absolute number, size, and presence of a non-proteinaceous material are analyzed in order to characterize the population of subvisible particles in the sample.

Additionally, the methods may include 1) in the interrogating the sample step that the at least one fluorescent dye includes a second fluorescent dye that stains a physical property of proteinaceous material in a manner that distinguishes a proteinaceous particle having the physical property from a proteinaceous particle not having the physical property, and the interrogation includes one or more wavelengths that can excite the second fluorescent dye; 2) in the collection data step that the collecting data further includes collecting data from a third fluorescence parameter, the third fluorescence parameter representing presence of a proteinaceous material having the physical property based upon fluorescence intensity emitted from the second fluorescent dye; and 3) in the data analysis step that the analyzing the data to define presence of the physical property to determine the fraction of counted, sized proteinaceous subvisible particles with or without the physical property, thereby characterizing the population of subvisible particles in the sample. In other aspects, an absolute number, size, and presence of non-proteinaceous subvisible material with and without a physical property are analyzed in order to characterize the population of subvisible particles in the sample.

Yet other aspects of the present specification disclose methods of characterizing a population of subvisible particles in a sample using a particle analyzer, the method comprising the steps of: a) calibrating a particle analyzer using a size standard; b) interrogating the sample as the sample passes through a sensing zone of the particle analyzer, the sample comprising at least one fluorescent dye, wherein the interrogation includes light of one or more wavelengths that can be scattered by the size standard and excite the at least one fluorescent dye, and wherein the at least one fluorescent dye includes a first fluorescent dye that stains proteinaceous material in a manner that distinguishes a proteinaceous particle from a non-proteinaceous particle; c) collecting data from at least one light scatter parameter and at least one fluorescence parameter, wherein the data collected from the at least one light scatter parameter represents a particle size based upon the size standard calibration, and wherein the data collected from the at least one fluorescence parameter includes a first fluorescence parameter representing presence of a proteinaceous material based upon fluorescence intensity emitted from the first fluorescent dye; and d) analyzing the data to define the particle size and presence of the proteinaceous material to determine size and presence of proteinaceous subvisible particles, thereby characterizing the population of subvisible particles in the sample. In other aspects, a size and presence of a non-proteinaceous material are analyzed in order to characterize the population of subvisible particles in the sample.

Additionally, the methods may include 1) in the interrogating the sample step that the sample further comprises a fluorescent counting standard, and the interrogation includes one or more wavelengths that can interrogate or excite the fluorescent counting standard; 2) in the collection data step that the at least one fluorescence parameter includes a second fluorescence parameter representing particle number based upon fluorescence intensity emitted from the fluorescent counting standard; and 3) in the data analysis step that analyzing the data to define the particle number to determine the absolute number of the sized proteinaceous subvisible particles, thereby characterizing the population of subvisible particles in the sample. In other aspects, an absolute number of a non-proteinaceous material is analyzed in order to characterize the population of subvisible particles in the sample.

Additionally, the methods may further include 1) in the interrogating the sample step that the at least one fluorescent dye includes a second fluorescent dye that stains a physical property of proteinaceaous material in a manner that distinguishes a proteinaceavus material having the physical property from a proteinaceous material not having the physical property, and the interrogation includes one or more wavelengths that can excite the second fluorescent dye; 2) in the collection data step that collecting data further includes collecting data from a third fluorescence parameter, the third fluorescence parameter representing presence of a proteinaceous material having the physical property based upon fluorescence intensity emitted from the second fluorescent dye; and 3) in the data analysis step that analyzing the data to define presence of the physical property to determine the fraction of counted, sized proteinaceous subvisible particles with or without the physical property, thereby characterizing the population of subvisible particles in the sample. In other aspects, an absolute number, size, and presence of non-proteinaceous subvisible material with and without a physical property are analyzed in order to characterize the population of subvisible particles in the sample.

BRIEF DESCRIPTION OF THE DRAWINGS

FIG. 3 also shows a bar graph (C) of proteinaceous subvisible particle number versus size distribution range from both a control sample (D-PBS) and a test sample (Abeta 1-42 fibrils).

FIG. 4 also shows data indicating that proteinaceous (SO+) and non-proteinaceous subvisible particles (SO−) can be discriminated from one another (C) or qualitatively compared to one another (D) based on fluorescent intensity due to SYPRO™ Orange (SO) staining. FIG. 4 further shows that data indicating that proteinaceous (SO+) and non-proteinaceous subvisible particles (SO−) can be discriminated and quantitatively compared to one another (E).

FIG. 5 also shows data indicating that proteinaceous subvisible particles having a β-sheet structure (ThT+) and proteinaceous subvisible particles lacking such a structure (ThT−) can be discriminated from one another based on fluorescent intensity due to Thioflavin T (ThT) staining (B). FIG. 5 also shows collected data can identify proteinaceous subvisible particles having a β-sheet structure from the total population of particles in the sample (C). FIG. 5 further shows a bar graph indicating the absolute number of total subvisible particles (Total events), proteinaceous subvisible particles (SO+), non-proteinaceous subvisible particles (SO−), and proteinaceous subvisible particles with a β-sheet structure (SO+ ThT+), classified based on the size distribution range for each particle (D).

FIG. 6 also shows that a plot of Side Scatter against Forward Scatter is first used to generate data that detects subvisible particles within a sample (B), and that Bis-ANS detection (a protein-specific dye) is plotted against Forward Scatter to discriminate between proteinaceous and non-proteinaceous subvisible particles (C). FIG. 6 also shows that proteinaceous subvisible particles were further characterized using 9-(2,2-Dicyanovinyl)julolidine (DCVJ) plotted against Forward Scatter (D); DCVJ specifically binds to cross-β structures and enables the identification of amyloid-like proteinaceous subvisible particles. FIG. 6 also shows backgating analyses of proteinaceous and non-proteinaceous subvisible particles (E).

DETAILED DESCRIPTION

Figure 1A:
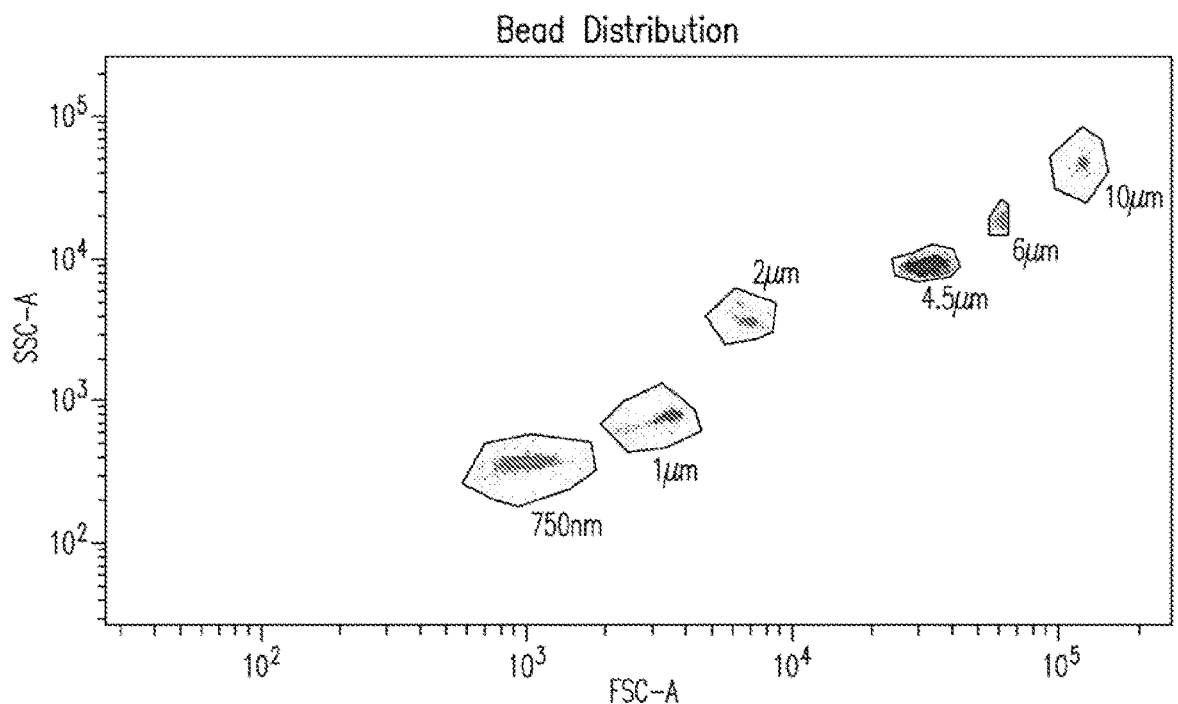
FIGS. 1A and 1B shows data representing particle size (A) and size distribution range (B) generated from forward light scatter and side light scatter parameters. For FIG. 1B the areas depicted by the different types of hatching represent particle sizes of less than about 0.75 µm, from about 0.75 µm to about 1.0 µm, from about 1.0 µm to about 2.0 µm, from about 2.0 µm to about 4.5 µm, from about 4.5 µm to about 6.0 µm, from about 6.0 µm to about 10 µm, and greater than about 10 µm.

Aspects of the present specification disclose, in part, a sample. A sample may comprise a test sample, such as, e.g., a pharmaceutical preparation. A pharmaceutical preparation may include a proteinaceous material. The proteinaceous material may be chemically synthesized, recombinantly produced, or purified from a natural source. A proteinaceous material may be an active pharmaceutical ingredient of the pharmaceutical preparation, and/or an adjuvant, a carrier, and/or an excipient used in the pharmaceutical preparation.

An active pharmaceutical ingredient can refer to any substance or mixture of substances intended to be used in the manufacture of a drug product and that, when used in the production of a drug, becomes an active ingredient in the drug product. Such substances are intended to furnish pharmacological activity or other direct effect in the diagnosis, cure, mitigation, treatment or prevention of disease or to affect the structure and function of the body. An active pharmaceutical ingredient can include, without limitation, an antibody, an enzyme, a toxin, or any other polypeptide or peptidomemetic designed to have a beneficial effect when given to an individual. An excipient can include, without limitation, an albumin.

An antibody refers to a molecule generated by an immune system that was made in response to a particular antigen that specifically binds to that antigen, and includes both naturally occurring antibodies and non-naturally occurring antibodies. An antibody can be a polyclonal antibody, a monoclonal antibody, a dimer, a multimer, a multispecific antibody, a humanized antibody, a chimeric antibody, bi-functional antibody, a cell-associated antibody like an Ig receptor, a linear antibody, a diabody, or a minibody, so long as the fragment exhibits the desired biological activity, and single chain derivatives of the same. An antibody can be a full-length immunoglobulin molecule comprising the $V_H$ and $V_L$ domains, as well as a light chain constant domain ($C_L$) and heavy chain constant domains, $C_{H1}$, $C_{H2}$ and $C_{H3}$, or an immunologically active fragment of a full-length immunoglobulin molecule, such as, e.g., a Fab fragment, a $F(ab')_2$ fragment, a Fc fragment, a Fd fragment, a Fv fragment. An antibody can be derived from any vertebrate species (e.g., human, goat, horse, donkey, murine, rat, rabbit, or chicken), and can be of any type (e.g., IgG, IgE, IgM, IgD, and IgA), class (e.g., IgA, IgD, IgE, IgG, and IgM) or subclass (IgG1, IgG2, IgG3, IgG4, IgA1 and IgA2). Currently there are over 30 antibody-based therapies approved by the Food and Drug Administration. These include Abciximab, Adalimumab, Alemtuzumab, Basiliximab, Belimumab, Bevacizumab, Brentuximab Vedotin, Canakinumab, Certolizumab pegol, Cetuximab, Daclizumab, Denosumab, Efalizumab, Eculizumab, Gemtuzumab ozogamicin, Golimumab, Ibritumomab tiuxetan, Infliximab, Ipilimumab, Motavizumab, Muronomab, Natalizumab, Ofatumumab, Omalizumab, Palivizumab, Panitumumab, Ranibizumab, Raxibacumab, Rituximab, Tocilizumab, Tositumomab, Trastuzumab, and Ustekinumab.

In an embodiment, an active pharmaceutical ingredient includes a toxin, like a cytotoxin or a non-cytotoxin. A cytotoxin is a substance that has a toxic (or killing) effect on cells, such as, e.g., necrosis or apoptosis, whereas a non-cytotoxin is a substance that has a non-toxic (non-killing) effect on cells, such as, e.g., inhibition of endocytosis, exocytosis, cytokinesis, karyokinesis. Non-limiting examples of a cytotoxin include a venom such as, e.g., a snake venom and a conch venom, a plant toxin such as, e.g., ricin, and abrin, a bacterial toxin such as, e.g., diphtheria toxin, and *Pseudomonas* exotoxin, and a viral toxin such as, e.g., a Shiga toxin. Non-limiting examples of a non-cytotoxin include a Clostridial toxin like a *C. botulinum* toxin, a *C. baratii* toxin, a *C. butyricum* toxin, and a *C. tetani*.

In an embodiment, an active pharmaceutical ingredient includes a blood protein like a blood coagulation protein, including both its inactive and active forms. Non-limiting examples of blood proteins include ADAMTS-13, α1-antiplasmin, α2-antiplasmin, antithrombin, antithrombin III, cancer procoagulant, erythropoietin, Factor II, Factor IIa, Factor V, Factor Va, Factor VI, Factor VIa, Factor VII, Factor VIIa, Factor VIII, Factor VIIIa, Factor IX, Factor IXa, Factor X, Factor Xa, Factor XI, Factor XIa, Factor XII, Factor XIIa, Factor XIII, Factor XIIIa, fibronectin, fibrinogen (Factor I), heparin cofactor II, high-molecular-weight kininogen (HMWK), intramuscular immunoglobulin, intravenous immunoglobulin, plasmin, plasminogen, plasminogen activator inhibitor-1 (PAI1), plasminogen activator inhibitor-2 (PAI2), prekallikrein, prostacyclin, protein C, active protein C (APC), protein S, protein Z, protein Z-related protease inhibitor, thrombomodulin, tissue factor (Factor III), Tissue factor pathway inhibitor (TFPI), tissue plasminogen activator (t-PA), urokinase, and Von Willebrand Factor.

In an embodiment, an active pharmaceutical ingredient includes an insulin.

The sample may also comprise a counting standard as disclosed herein, at least one fluorescent dye disclosed herein, or both a counting standard and at least one fluorescent dye.

A sample may comprise a control sample. A control sample may be used to assess the presence of extraneous subvisible particles such as, e.g., dust particles, glass particles, leachable particles, and/or oil particles. The data collected from this control sample may then be subtracted from the test sample data.

The present specification discloses, in part, a population of subvisible particles. A subvisible particle is undissolved particulate matter, other than gas bubbles, that cannot be observed by visual inspection. Although no strict size limit can be assigned for when particles become visible to the human eye, it is generally recognized that particles more than 100-200 µm in size are detected with relatively high probability under appropriate testing conditions. As such, the size of a subvisible particle may be less than or equal to 200 µm. Subvisible particles have different origins. They may be pure protein aggregates; glass particles; a leachable particle like Tungsten, silicon oil, metals; and also complexes of these leachable particles with proteins and protein aggregates. As such, subvisible particles may be proteinaceous, non-proteinaceous, or both.

In aspects of this embodiment, a method disclosed herein may characterize a subvisible particle having a size that is, e.g., less than or equal to 200 µm, less than or equal to 150 µm, less than or equal to 100 µm, less than or equal to 75 µm, less than or equal to 50 µm, less than or equal to 25 µm, less than or equal to 10 µm, less than or equal to 7.5 µm, less than or equal to 5 µm, less than or equal to 2.5 µm, less than or equal to 1 µm, less than or equal to 0.75 µm, less than or equal to 0.5 µm, or less than or equal to 0.1 µm. In other aspects of this embodiment, a method disclosed herein may characterize a subvisible particle having a size between, e.g., about 0.05 µm to about 200 µm, about 0.05 µm to about 150 µm, about 0.05 µm to about 100 µm, about 0.05 µm to about 75 µm, about 0.05 µm to about 50 µm, about 0.05 µm to about 20 µm, about 0.1 µm to about 200 µm, about 0.1 µm to about 150 µm, about 0.1 µm to about 100 µm, about 0.1 µm to about 75 µm, about 0.1 µm to about 50 µm, or about 0.1 µm to about 20 µm.

Proteinaceous subvisible particles can be relatively large assemblies that contain thousands to millions of protein molecules. In aspects of this embodiment, a method disclosed herein may characterize a proteinaceous subvisible particle having a size that is, e.g., less than or equal to 200 µm, less than or equal to 150 µm, less than or equal to 100 µm, less than or equal to 75 µm, less than or equal to 50 µm, less than or equal to 25 µm, less than or equal to 10 µm, less than or equal to 7.5 µm, less than or equal to 5 µm, less than or equal to 2.5 µm, less than or equal to 1 µm, less than or equal to 0.75 µm, less than or equal to 0.5 µm, or less than or equal to 0.1 µm. In other aspects of this embodiment, a method disclosed herein may characterize a proteinaceous subvisible particle having a size between, e.g., about 0.05 µm to about 200 µm, about 0.05 µm to about 150 µm, about 0.05 µm to about 100 µm, about 0.05 µm to about 75 µm, about 0.05 µm to about 50 µm, about 0.05 µm to about 20 µm, about 0.1 µm to about 200 µm, about 0.1 µm to about 150 µm, about 0.1 µm to about 100 µm, about 0.1 µm to about 75 µm, about 0.1 µm to about 50 µm, or about 0.1 µm to about 20 µm.

Non-proteinaceous subvisible particles can be inorganic or organic matter and include, without limitation, glass particles, metal particles, and an oil. In aspects of this embodiment, a method disclosed herein may characterize a non-proteinaceous subvisible particle having a size that is, e.g., less than or equal to 200 µm, less than or equal to 150 µm, less than or equal to 100 µm, less than or equal to 75 µm, less than or equal to 50 µm, less than or equal to 25 µm, less than or equal to 10 µm, less than or equal to 7.5 µm, less than or equal to 5 µm, less than or equal to 2.5 µm, less than or equal to 1 µm, less than or equal to 0.75 µm, less than or equal to 0.5 µm, or less than or equal to 0.1 µm. In other aspects of this embodiment, a method disclosed herein may characterize a non-proteinaceous subvisible particle having a size between, e.g., about 0.05 µm to about 200 µm, about 0.05 µm to about 150 µm, about 0.05 µm to about 100 µm, about 0.05 µm to about 75 µm, about 0.05 µm to about 50 µm, about 0.05 µm to about 20 µm, about 0.1 µm to about 200 µm, about 0.1 µm to about 150 µm, about 0.1 µm to about 100 µm, about 0.1 µm to about 75 µm, about 0.1 µm to about 50 µm, or about 0.1 µm to about 20 µm.

The present specification discloses, in part, a particle analyzer. A particle analyzer includes a flow cytometer. Flow cytometry can combine light scattering from particles and light emission from fluorochromic molecules to generate specific multiparameter data sets for particles in the range of about 0.02 µm to about 100 µm. One unique feature of flow cytometry is that it can measure light scattering and fluorescence emission properties of thousands of individual particles per second. The sample can be injected into a flow chamber where the particles are hydro-dynamically focused in a sheath of fluid that forces the particles into a single-file line in the center of the fluid stream. Each particle then passes through a sensing zone where an optimally focused light source interrogates the particle. Lasers are most often used as the light source in flow cytometry. As the light source interrogates the passing particle, the particle scatters light and, if having fluorescent properties, the particle can also be excited to a higher energy state where it releases energy as a photon of light with specific spectral properties.

Flow cytometry analysis of a particle yields multiparameter data corresponding to light scatter, light absorption, and fluorescence intensity. A standard flow cytometer can typically differentiate light scatter (LS) as Forward Light Scatter (FLS), Side Light Scatter (SLS) and Reverse Light Scatter (RLS) and detect up to four different fluorescent intensity emissions (FL1-FL4). Scattered and emitted light parameters from each particle are converted to electrical pulses by optical detectors. Collimated (parallel light waveforms) light is picked up by confocal lenses focused at the intersection point of the particle and the light source. Light is sent to different detectors by using optical filters. The most common type of detector used in flow cytometry is the photomultiplier tube (PMT). The electrical pulses originating from light detected by the PMTs are then processed by a series of linear and log amplifiers. Logarithmic amplification is most often used to measure fluorescence intensity. This type of amplification expands the scale for weak signals and compresses the scale for "strong" or specific fluorescence signals. After the different signals or pulses are amplified they are processed by an Analog to Digital Converter (ADC) which in turn allows for events to be plotted on a graphical scale. Typical scales include a one-parameter histogram and a two-parameter histogram.

Flow cytometry data outputs are stored in the form of computer files. Data corresponding to one sample can be stored as a listmode file and/or histogram file. Listmode files contain a complete listing of all events corresponding to all the parameters collected, as specified by a user-defined acquisition protocol. The acquisition protocol serves as a template that defines which specific parameters (e.g., light scatter and/or fluorescence) are collected and how these collected parameters are displayed. In addition, an acquisition protocol serves to determine how the data is gated, and contains all the regions from which statistics can be generated. In addition, protocols contain other specific information that serves as direct interface between the computer workstation and the cytometer including those pertaining to high voltage settings for the PMT detectors, gains for amplification of linear parameters, sample flow rates, fluorescence compensation, and discrimination settings.

Histogram files can be in the form of one-parameter or two-parameter files. Histogram files consist of a list of the events corresponding to the graphical display specified in your acquisition protocol. A one-parameter histogram is a graph of cell count on the y-axis and the measurement parameter on the x-axis. A two-parameter histogram is a graph representing two measurement parameters, on the x- and y-axes, and cell count height on a density gradient. This is similar to a topographical map. Particle counts are shown by dot density or by contour plot.

The process of separating cells using flow cytometry multiparameter data is referred to as sorting. A flow cytometer capable of cell sorting will include a tunable transducer which permits the breaking of the fluid sheath into individual droplets that encapsulate a single particle, electric charge delays for charging individual droplets, deflection plates for deflecting individually charged droplets into collection tubes, and software settings for defining sorting criteria, these include regions defining populations to be sorted.

The present specification discloses, in part, calibrating a particle analyzer using a size standard. A size standard comprising a calibrated suspension of particles of one or more known sizes with each size having a mean diameter. A size standard is used to define size distribution ranges that will allow sizing of the subvisible particles present in a sample. Particles representing a particular size may be of any regular (geometric) or irregular shape, may be made from any material, and may be fluorescent or non-fluorescent. Mean particle diameters present in a size standard include, without limitation, 0.5 µm, 1.0 µm, 2.0 µm, 4.0 µm, 6 µm, 10 µm, 15 µm, 20 µm, 30 µm, 40 µm, 50 µm, 60 µm, 70 µm, 80 µm, 90 µm, 100 µm, 125 µm, 150 µm, 175 µm, 200 µm, or any combination thereof and in any range found between any of these values. Non-limiting examples of a size standard include Fluoresbright Size Calibration Kit I and II (Polysciences, Inc., Warrington, PA), Flow Cytometry Size Calibration Kit (Invitrogen, Corp., Carlsbad, CA), ChromoSphere-T Certified Size Standards (Thermo Fisher Scientific Inc., Waltham, MA), 3000 Series Nanosphere (Thermo Fisher Scientific Inc., Waltham, MA), 8000 Series Silica Particle Size Standards (Thermo Fisher Scientific Inc., Waltham, MA), and Size Calibration Standards Kit (Bangs Laboratories, Inc., Fishers, IN).

A particle analyzer can be calibrated by running a sample comprising a size standard disclosed herein and collecting light scatter parameters. The voltage of the photomultiplier tube (PMT) may be adjusted in order to collect size information. For example, increasing the PMT voltage allows for detection of smaller sizes. The upper size limitation is typically dependant on the diameter of the tubing used in the particle analyzer, and thus may vary. In aspects of this embodiment, the upper size limit may be, e.g., 150 µm, 175 µm, 200 µm, 225 µm, 250 µm, 275 µm, or 300 µm. The light scatter data is collected based on particle size and these data are used to create a gating database in order to set gates of defined size distribution ranges. In an aspect of this embodiment, the size distribution range is for particles that are e.g., less than or equal to 150 µm, less than or equal to 175 µm, less than or equal to 200 µm, less than or equal to 225 µm, less than or equal to 250 µm, less than or equal to 275 µm, or less than or equal to 300 µm.

In another aspect the size distribution ranges are, e.g., less than 0.75 µm, 0.75-1 µm, 1-2 µm, 2-4 µm, 4-6 µm, 6-8 µm, 8-10 µm, 10-20 µm, 20-30 µm, 30-40 µm, 40-50 µm, 50-60 µm, 60-70 µm, 70-80 µm, 80-90 µm, 90-100 µm, 100-150 µm, or any combination thereof. In yet another aspect the size distribution ranges are, e.g., 0.10-0.25 µm, 0.25-0.50 µm, 0.50-0.75 µm, 0.75-1 µm, 1-2 µm, 2-4 µm, 4-6 µm, 6-8 µm, 8-10 µm, 10-20 µm, 20-30 µm, 30-40 µm, 40-50 µm, 50-60 µm, 60-70 µm, 70-80 µm, 80-90 µm, 90-100 µm, 100-150 µm, or any combination thereof. In another aspect the size distribution ranges are, e.g., less than 0.75 µm, 0.75-1 µm, 1-2 µm, 2-4.5 µm, 4.5-6 µm, 6-10 µm, more than 10 µm, or any combination thereof. In yet another aspect the size distribution ranges are, e.g., less than 0.10-0.25 µm, 0.25-0.50 µm, 0.50-0.75 µm, 0.75-1 µm, 1-2 µm, 2-4.5 µm, 4.5-6 µm, 6-10 µm, more than 10 µm, or any combination thereof. This gating database may be stored by the particle analyzer for subsequent analysis of a test sample.

The present specification discloses, in part, interrogating a sample as the sample passes through a sensing zone of a particle analyzer. Interrogation occurs when a particle passes through an optimally focused light source causing the particle to scatter light and/or emit a photon or photons of light having specific spectral properties. Interrogation includes light of one or more wavelengths that can be scattered by a particle or be used to excite a particle having fluorescent properties. Which particular light wavelengths are used to interrogate a particle can be user-defined and based, in part, on the particular size desired to be detected, the particular excitation spectrum of a particle, the peak excitation wavelength of the particle, the particular emission spectrum of a particle, the peak emission wavelength of the particle, the degree of overlap between two or more particular excitation spectra, and the degree of overlap between two or more particular emission spectra.

In an aspect of this embodiment, the interrogation may include one or more wavelengths that can be scattered by a size standard. In another aspect of this embodiment, the interrogation may include one or more wavelengths that can be scattered by a size standard and excite at least one fluorescent dye. In yet another aspect of this embodiment, the interrogation may include one or more wavelengths that can be scattered by or excite a fluorescent counting standard, and scattered by or excite at least one fluorescent dye. In still another aspect of this embodiment, the interrogation may include one or more wavelengths that can be scattered by a size standard, scattered by or excite a fluorescent counting standard, and scattered by or excite at least one fluorescent dye.

Aspects of the present specification disclose, in part, at least one fluorescent dye. A fluorescent dye refers to a compound that upon excitation absorbs light energy of a certain wavelength and emits light energy of a different wavelength. In an aspect of this embodiment, a method disclosed herein uses a single fluorescent dye. In another aspect of this embodiment, a method disclosed herein uses a plurality of fluorescent dyes. In yet other aspects of this embodiment, a method disclosed herein uses a first fluorescent dye and a second fluorescent dye. In still other aspects of this embodiment, a method disclosed herein uses a first fluorescent dye, a second fluorescent dye, and a third fluorescent dye. In other aspects of this embodiment, a method disclosed herein uses a first fluorescent dye, a second fluorescent dye, a third fluorescent dye, and a fourth fluorescent dye. In yet other aspects of this embodiment, a method disclosed herein uses a first fluorescent dye and optionally a second fluorescent dye, a third fluorescent dye, a fourth fluorescent dye, a fifth fluorescent dye, a sixth fluorescent dye, a seventh fluorescent dye, an eighth fluorescent dye, a ninth fluorescent dye, and/or a tenth fluorescent dye. In still other aspects of this embodiment, a method disclosed herein uses a first fluorescent dye and a second fluorescent dye, and optionally a third fluorescent dye, a fourth fluorescent dye, a fifth fluorescent dye, a sixth fluorescent dye, a seventh fluorescent dye, an eighth fluorescent dye, a ninth fluorescent dye, and/or a tenth fluorescent dye.

A fluorescent dye disclosed herein encompass dyes which can emit in a variety of spectra, including ultraviolent, visible (including violet, blue, cyan, green, yellow, orange, and red), near infrared, medium infrared, and far infrared. A fluorescent dye includes without limitation, an acridine dye and its derivatives, an arylmethine dye and its derivatives, a coumarin dye and its derivatives, a cyanine dye and its derivatives, a naphthalene dye and its derivatives, an o-phthaldehyde dye and its derivatives, an oxadiazole dye and its derivatives, an oxazine dye and its derivatives, a phycoerythrin dye and its derivatives, a phycocyanin dye and its derivatives, a pyrene dye and its derivatives, a pyridyloxazole dye and its derivatives, a squarylium dye and its derivatives, a tetrapyrrole dye and its derivatives, and a xanthene dye and its derivatives. These and other dyes are known to a person of skill in the art.

A fluorescent dye useful to practice the methods disclosed herein may exhibit an excitation spectrum in the ultraviolet, visible, near infrared, medium infrared, or far infrared spectrums. In an aspect of this embodiment, a fluorescent dye useful to practice the methods disclosed herein may exhibit an excitation spectrum within the range of about 300 nm to about 800 nm. In an aspect of this embodiment, a fluorescent dye useful to practice the methods disclosed herein may exhibit an excitation spectrum within the range of about 300 nm to about 635 nm. In aspects of this embodiment, a fluorescent dye useful to practice the methods disclosed herein may exhibit an excitation spectrum in the range of about 300 nm to about 350 nm, about 350 nm to about 380 nm, about 380 nm to about 450 nm, about 420 nm to about 460 nm, about 450 nm to about 495 nm, about 460 nm to about 500 nm, about 495 nm to about 570 nm, about 500 nm to about 520 nm, about 520 nm to about 550 nm, about 550 nm to about 740 nm, about 570 nm to about 590 nm, about 590 nm to about 620 nm, about 620 nm to about 750 nm, or about 750 nm to about 800 nm. In yet other aspects of this embodiment, a fluorescent dye useful to practice the methods disclosed herein may exhibit an peak excitation wavelength in the range of about 300 nm to about 350 nm, about 350 nm to about 380 nm, about 380 nm to about 450 nm, about 420 nm to about 460 nm, about 450 nm to about 495 nm, about 460 nm to about 500 nm, about 495 nm to about 570 nm, about 500 nm to about 520 nm, about 520 nm to about 550 nm, about 550 nm to about 740 nm, about 570 nm to about 590 nm, about 590 nm to about 620 nm, about 620 nm to about 750 nm, or about 750 nm to about 800 nm. In still other aspects of this embodiment, a fluorescent dye useful to practice the methods disclosed herein may exhibit an peak excitation wavelength of about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, or about 630 nm.

A fluorescent dye useful to practice the methods disclosed herein may exhibit an emissions spectrum in the ultraviolet, visible, near infrared, medium infrared, or far infrared spectrums. In another aspect of this embodiment, a fluorescent dye useful to practice the methods disclosed herein may exhibit an emission spectrum within the range of about 300 nm to about 800 nm. In yet another aspect of this embodiment, a fluorescent dye useful to practice the methods disclosed herein may exhibit an emission spectrum within the range of about 385 nm to about 800 nm. In aspects of this embodiment, a fluorescent dye useful to practice the methods disclosed herein may exhibit an emission spectrum in the range of about 300 nm to about 350 nm, about 350 nm to about 380 nm, about 380 nm to about 450 nm, about 420 nm to about 460 nm, about 450 nm to about 495 nm, about 460 nm to about 500 nm, about 495 nm to about 570 nm, about 500 nm to about 520 nm, about 520 nm to about 550 nm, about 550 nm to about 740 nm, about 570 nm to about 590 nm, about 590 nm to about 620 nm, about 620 nm to about 750 nm, or about 750 nm to about 800 nm. In yet other aspects of this embodiment, a fluorescent dye useful to practice the methods disclosed herein may exhibit an peak emission wavelength in the range of about 300 nm to about 350 nm, about 350 nm to about 380 nm, about 380 nm to about 450 nm, about 420 nm to about 460 nm, about 450 nm to about 495 nm, about 460 nm to about 500 nm, about 495 nm to about 570 nm, about 500 nm to about 520 nm, about 520 nm to about 550 nm, about 550 nm to about 740 nm, about 570 nm to about 590 nm, about 590 nm to about 620 nm, about 620 nm to about 750 nm, or about 750 nm to about 800 nm. In still other aspects of this embodiment, a fluorescent dye useful to practice the methods disclosed herein may exhibit an peak emission wavelength of about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, about 630 nm, about 640 nm, about 650 nm, about 660 nm, about 670 nm, about 680 nm, about 690 nm, about 700 nm, about 710 nm, about 720 nm, about 730 nm, about 740 nm, about 750 nm, about 760 nm, about 770 nm, about 780 nm, about 790 nm, or about 800 nm.

A fluorescent dye disclosed herein is selected based on its ability to stains subvisible particles, a subset thereof like proteinaceous subvisible particles or non-proteinaceous subvisible particles, or a composition or property present on subvisible particles or a subset thereof like proteinaceous subvisible particles or non-proteinaceous subvisible particles. As used herein, the term "stains" when used in reference to a fluorescent dye refers to a fluorescent dye which will absorb light energy of a certain wavelength only when associated with material the user desires to be detected, will emit light energy of a certain wavelength only when associated with material the user desires to be detected, or will absorb light energy of a certain wavelength and emit light energy of a different wavelength only when associated with material the user desires to be detected. If a fluorescent dye associates with material the user does not wish to be detected, then the dye either doesn't absorb light energy and/or doesn't emit light energy, or emits light energy in a manner that a particle analyzer can distinguish between the fluorescence emitted by the fluorescent dye associated with material the user desires to be detected and the fluorescence emitted by the fluorescent dye associated with the material the user does not wish to be detected.

In one aspect of this embodiment, the at least one fluorescent dye may include a first fluorescent dye that stains proteinaceaous material in a manner that distinguishes a proteinaceaous particle from a non-proteinaceaous particle. As used herein, the term "stains" when used in reference to a first fluorescent dye for proteinaceaous material refers to a first fluorescent dye which will absorb light energy of a certain wavelength only when associated with proteinaceaous material, will emit light energy of a certain wavelength only when associated with proteinaceaous material, or will absorb light energy of a certain wavelength and emit light energy of a different wavelength only when associated with proteinaceous material. If a first fluorescent dye associates with non-proteinaceous material, then the dye either doesn't absorb light energy and/or doesn't emit light energy, or emits light energy in a manner that a particle analyzer can distinguish between the fluorescence emitted by the first fluorescent dye associated with proteinaceous material and the fluorescence emitted by the first fluorescent dye associated with non-proteinaceous material.

In another aspect of this embodiment, the at least one fluorescent dye may include a first fluorescent dye that stains non-proteinaceaous material in a manner that distinguishes a non-proteinaceaous particle from a proteinaceaous particle. As used herein, the term "stains" when used in reference to a first fluorescent dye for non-proteinaceaous material refers to a first fluorescent dye which will absorb light energy of a certain wavelength only when associated with non-proteinaceous material, will emit light energy of a certain wavelength only when associated with non-proteinaceaous material, or will absorb light energy of a certain wavelength and emit light energy of a different wavelength only when associated with non-proteinaceaous material. If a first fluorescent dye associates with proteinaceous material, then the dye either doesn't absorb light energy and/or doesn't emit light energy, or emits light energy in a manner that a particle analyzer can distinguish between the fluorescence emitted by the first fluorescent dye associated with non-proteinaceaous material and the fluorescence emitted by the first fluorescent dye associated with proteinaceous material.

Detection and distinction of a fluorescent dye associated with material the user desires to be detected may be based on, e.g., changes in fluorescent intensity, changes in the excitation spectrum like peak excitation wavelength, or changes in the emissions spectrum like peak emission wavelength. In one aspect of this embodiment, detection and distinction of proteinaceous material based on first fluorescent dye staining may be based on, e.g., changes in fluorescent intensity, changes in the excitation spectrum like peak excitation wavelength, or changes in the emissions spectrum like peak emission wavelength. In another aspect of this embodiment, detection and distinction of non-proteinaceous material based on first fluorescent dye staining may be based on, e.g., changes in fluorescent intensity, changes in the excitation spectrum like peak excitation wavelength, or changes in the emissions spectrum like peak emission wavelength.

Non-limiting examples of a first fluorescent dye that stains proteinaceaous material and may be used to distinguish proteinaceaous material from non-proteinaceaous material include styryl dye or merocyanine dye like SYPRO® Ruby, SYPRO® Tangerine, SYPRO® Orange (Invitrogen Corp., Carlsbad, CA) and SYPRO® Red (Invitrogen Corp., Carlsbad, CA); coumarin derivatives like 3-(2- benzothiazolyl-7-(diethylamino)-coumarin (BTDEC), 3-(2-benzimidazolyl)-7-(diethylamino)-coumarin (BIDEC), 3-(2-benzimidazolyl)-7-coumarin (BIC), 3-(2-benzimidazolyl)-7-(dipropylamino)-coumarin (BIDPC), 3-(2-benzoxazolyl)-7-(diethylamino)-coumarin (BODEC), 3-(6-methyl-2-benzoxazolyl)-7-(diethylamino)-coumarin (MBODEC), 3-(diethylamino)-7-imino-7H-(1)benzopyrano(3',2':3,4) pyrido(1,2-a)benzimidazole-6-carbonitrile (DIBPBC), 3-(diethylamino)-7-oxo-7H-(1)benzopyrano(3',2':3,4) (DOBPBC); dipyrrometheneboron difluoride and its derivatives, described in, e.g., U.S. Pat. No. 4,774,339 which is hereby incorporated by reference in its entirety; photoluminescent metal complexes, described in, e.g., US 2009/0131640 which is hereby incorporated by reference in its entirety; and hydroxyquinolone and its derivatives, described in, e.g., US 2007/0281360 which is hereby incorporated by reference in its entirety. The peak excitation and emission wavelengths for fluorescent dyes useful as a first fluorescent dye disclosed herein are listed in Table 1. Other fluorescent dyes useful as a first fluorescent dye disclosed herein are known by a person skilled in the art.

TABLE 1

Fluorescent Dye Peak Excitation and Emission Wavelengths[a]

| Fluorescent Dye | Peak Excitation λ (nm) | Peak Emission λ (nm) |
| --- | --- | --- |
| SYPRO ® Ruby | 450 | 610 |
| SYPRO ® Orange | 470 | 570 |
| SYPRO ® Tangerine | 490 | 640 |
| SYPRO ® Red | 550 | 630 |
| BTDEC | 474 | 511 |
| BIDEC | 457 | 497 |
| BIC | 456 | 497 |
| BIDPC | 456 | 497 |
| Bis-ANS | 395 | 500 |
| BODEC | 460 | 502 |
| MBODEC | 458 | 501 |
| DIBPBC | 554 | 580 |
| DOBPBC | 559 | 584 |
| Dipyrrometheneboron difluoride compound 1 | 490 | 503 |
| Dipyrrometheneboron difluoride compound 2 | 505 | 515 |
| Dipyrrometheneboron difluoride compound 3 | 528 | 548 |
| Dipyrrometheneboron difluoride compound 4 | 564 | 591 |
| Dipyrrometheneboron difluoride compound 5 | 606 | 633 |
| Dipyrrometheneboron difluoride compound 6 | 644 | 668 |
| Dipyrrometheneboron difluoride compound 7 | 503 | 519 |
| Dipyrrometheneboron difluoride compound 8 | 491 | 503 |
| Dipyrrometheneboron difluoride compound 9 | 490 | 503 |
| Dipyrrometheneboron difluoride compound 10 | 665 | 676 |
| LUCY-506 | 506 | 520 |
| LUCY-565 | 565 | 588 |
| LUCY-569 | 569 | 585 |
| Flamingo Pink | 532 | 555 |
| Deep Purple | 530 | 600 |
| ProQ Emerald 300 | 280 | 530 |
| Vistra Green | 490 | 520 |
| Oregon Green | 496 | 524 |
| SYBR Gold | 300 or 495 | 537 |
| SYBR Green I | 290, 380, or 497 | 520 |
| SYBR Green II | 254 or 497 | 520 |
| Radiant Red | 300 or 495 | 630 |

[a]Indicated values of excitation and emission maximum are average values, but a person of skill understands that these values can vary depending on conditions, such as, e.g., solution pH, ionic strength, dye concentration and/or dye conformation.

Non-limiting examples of a first fluorescent dye that stains non-proteinaceous material and may be used to distinguish non-proteinaceous material from proteinaceous material include lipophilic dyes. Lipophilic dyes useful in the methods disclosed herein include, but are not limited to, carbocyanine lipophilic dyes, lipophilic aminostyryl dyes, amphiphilic styryl dyes, dialkylaminostyryl dyes, amphiphilic probes, nonpolar probes, membrane probes, and lipophilic cation probes. Carbocyanine lipophilic dyes include, without limitation, an octadecyl($C_{18}$) indocarbocyanine like DiI and DiD, a thiacarbocyanine like (DiS) and an oxacarbocyanine like DiO. Lipophilic aminostyryl dyes include, without limitation, 4-Di-10-ASP (D291); DiA, D3883 and FAST DiA (Molecular Probes, Inc., Eugene, OR). Amphiphilic probes include, without limitation, probes comprising derivatives of a rhodamine, a fluorescein, a coumarin, 1,6-Diphenyl-1,3,5-hexatriene (DPH) or DPH derivatives with a lipophilic "tail." Non-limiting examples of such amphiphilic probes include octadecyl rhodamine B; fluoresceins, such as, e.g., 5-Dodecanoylaminofluorescein, 5-hexadecanoyl-aminofluorescein, 5-octadecanoyl-aminofluorescein and the octadecyl ester of fluorescein; 4-heptadecyl-7-hydroxycoumarin; 1,6-Diphenyl-1,3,5-hexatriene (DPH), 1-(4-trimethylammoniumphenyl)-6-phenyl-1,3,5-hexatriene p-toluenesulfonate (TMA-DPH), N-((4-(6-phenyl-1,3,5-hexatrienyl)phenyl)propyl)trimethylammonium p-toluenesulfonate (TMAP-DPH), Dapoxyl sulfonic acid and 3-(4-(6-phenyl)-1,3,5-hexatrienyl)phenylpropionic acid (DPH propionic acid). Nonpolar probes include, without limitation, probes comprising a BODIPY molecule with a lipophilic "tail." Non-limiting examples of such nonpolar probes include BODIPY 493/503, BODIPY 505/515, BODIPY 665/676, BODIPY FL C5-ceramide and CellTrace BODIPY TR methyl ester, a phenoxazine dye nile red, a 1,3-Bis-(1-pyrene)propane or bimane azide molecule with a lipophilic "tail." Membrane probes include, without limitation, dapoxyl derivatives, such as, e.g., dapoxyl sulfonic acid; 6-propionyl-2-dimethylaminonaphthalene (prodan), 6-dodecanoyl-2-dimethylaminonaphthalene (laurdan), 6-acryloyl-2-dimethylaminonaphthalene (acrylodan), 6-bromoacetyl-2-dimethylaminonaphthalene (badan); anilinonaphthalenesulfonate (ANS) and derivatives thereof, such as, e.g., 1-anilinonaphthalene-8-sulfonic acid (1,8-ANS), 2-anilinonaphthalene-6-sulfonic acid (2,6-ANS), 2-(p-toluidinyl)naphthalene-6-sulfonic acid (2,6-TNS), 4,4'-dianilino-1,1'-binaphthyl-5,5'-disulfonic acid (bis-ANS); 4-(dicyanovinyl)julolidine (DCVJ); and 4-amino-4'-benzamidostilbene-2,2'-disulfonic acid (MBDS or BADS). Lipophilic cations include, without limitation, octadecyl rhodamine, and FM® dyes such as N-(3-triethylammoniumpropyl)-4-(4-(dibutylamino)styryl)pyridinium dibromide (FM® 1-43), N-(3-triethylammoniumpropyl)-4-(4-(dipentylamino)styryl)pyridinium dibromide (FM® 1-84), N-(3-triethylammoniumpropyl)-4-(4-(diethylamino)styryl)pyridinium dibromide (FM® 2-10) N-(3-triethylammoniumpropyl)-4-(6-(4-(diethylamino)phenyl) hexatrienyl) pyridinium dibromide (FM® 4-64), N-(3-trimethylammoniumpropyl)-4-(6-(4-(diethylamino)phenyl) hexatrienyl) pyridinium dibromide (FM® 5-95), N-(3-triethylammoniumpropyl)-4-(4-(diethylamino)phenyl) butadienyl) pyridinium dibromide (RH 414) and derivatives thereof (Molecular Probes, Inc., Eugene, OR); fluorescent phospholipid conjugates such as NBD-PE (Molecular Probes, Inc., Eugene, OR); lipid raft probes, which are detergent-insoluble. The peak excitation and emission wavelengths for lipophilic dyes useful as a first fluorescent dye disclosed herein are listed in Table 2. Other lipophilic dyes useful as a first fluorescent dye disclosed herein are known by a person skilled in the art.

TABLE 2

Excitation and Emission Maxima of Exemplary Lipophilic Dyes

| Cat No. | Dye | Excitation maxima (nm) | Emission maxima (nm) |
|---|---|---|---|
| DiO and analogs | | | |
| D3898 | FAST DiO | 484 | 499 |
| D275 | $DiOC_{18}(3)$ "DiO" | 484 | 501 |
| D1125 | $DiOC_{16}(3)$ | 484 | 501 |
| D7778 | $SP\text{-}DiOC_{18}(3)$ | 497 | 513 |
| DiA and analogs | | | |
| D3883 | 4-Di-16-ASP "DiA" | 491 | 613 |
| D3897 | FAST DiA oil | 492 | 612 |
| D7758 | FAST DiA | 492 | 612 |
| D291 | 4-Di-10-ASP | 492 | 612 |
| DiS and DiI and analogs | | | |
| B413 | $DiSBAC_2(3)$ | 535 | 560 |
| D282/D3911 | $DiIC_{18}(3)$ "DiI" | 549 | 565 |
| D384 | $DiIC_{16}(3)$ | 549 | 565 |
| D383 | $DiIC_{12}(3)$ | 549 | 565 |
| D3899 | FAST DiI oil | 549 | 564 |
| D7756 | FAST DiI | 549 | 564 |
| D3886 | $\Delta^9$-DiI oil | 549 | 564 |
| F6999 | FM ®DiI | 553 | 570 |
| C7000/C7001 | CellTracker CM-DiI | 553 | 570 |
| D7776 | $DiIC_{18}(3)\text{-}DS$ | 555 | 570 |
| D7777 | $SP\text{-}DiIC_{18}(3)$ | 556 | 573 |
| D7766 | $Br_2\text{-}DiIC_{18}(3)$ | 558 | 575 |
| D7779 | $5,5'\text{-}Ph_2\text{-}DiIC_{18}(3)$ | 576 | 599 |
| DiD and analogs | | | |
| D307 | $DiIC_{18}(5)$ oil "DiD" | 644 | 665 |
| D7757 | $DiIC_{18}(5)$ "DiD" | 644 | 663 |
| D12730 | $DiIC_{18}(5)\text{-}DS$ | 650 | 670 |
| DiR and analogs | | | |
| D12731 | $DiIC_{18}(7)$ "DiR" | 748 | 780 |
| Miscellaneous Molecules | | | |
| D202 | DPH | 300 | 452 |
| T204 | TMA-DPH | 355 | 430 |
| T53 | 2,6-TNS | 318 | 443 |
| D250 | laurdan | 364 | 497 |
| B153 | bis-ANS | 395 | 500 |
| FM ® and analogs | | | |
| T3163 | FM ® 1-43 | 479 | 598 |
| T3164 | FM ® 1-84 | 510 | 625 |
| T7508 | FM ® 2-10 | 506 | 620 |
| T3166 | FM ® 4-64 | 506 | 750 |
| T23360 | FM ® 5-95 | 560 | 734 |
| T1111 | RH 414 | 500 | 635 |

The use of a fluorescent dye that distinguishes proteinaceous particles from non-proteinaceous particles enables the detection of subvisible particles below 1 μm from background noise. In aspects of this embodiment, a fluorescent dye that stains proteinaceous particles as disclosed herein enables the detection of subvisible particles having a size of, e.g., less than or equal to 1 μm, less than or equal to 900 nm, less than or equal to 800 nm, less than or equal to 750 nm, less than or equal to 700 nm, less than or equal to 600 nm, less than or equal to 500 nm, less than or equal to 400 nm, less than or equal to 300 nm, less than or equal to 250 nm, less than or equal to 200 nm, or less than or equal to 100 nm. In other aspects, a fluorescent dye that stains proteinaceous particles as disclosed herein enables the detection of subvisible particles of between, e.g., about 100 nm to about 1 μm, about 250 nm to about 1 μm, about 500 nm to about 1 μm, about 750 nm to about 1 μm, about 100 nm to about 750 nm, about 250 nm to about 750 nm, or about 500 nm to about 750 nm.

In other aspects of this embodiment, a fluorescent dye that stains non-proteinaceous particles as disclosed herein enables the detection of subvisible particles having a size of, e.g., less than or equal to 1 μm, less than or equal to 900 nm, less than or equal to 800 nm, less than or equal to 750 nm, less than or equal to 700 nm, less than or equal to 600 nm, less than or equal to 500 nm, less than or equal to 400 nm, less than or equal to 300 nm, less than or equal to 250 nm, less than or equal to 200 nm, or less than or equal to 100 nm. In other aspects, a fluorescent dye that stains non-proteinaceous particles as disclosed herein enables the detection of subvisible particles of between, e.g., about 100 nm to about 1 μm, about 250 nm to about 1 μm, about 500 nm to about 1 μm, about 750 nm to about 1 μm, about 100 nm to about 750 nm, about 250 nm to about 750 nm, or about 500 nm to about 750 nm.

In another aspect of this embodiment, the at least one fluorescent dye may include a second fluorescent dye that stains a physical property of proteinaceous material in a manner that distinguishes a proteinaceous material having the physical property from a proteinaceous material not having the physical property. As used herein, the term "stains" when used in reference to a second fluorescent dye for a physical property of proteinaceous material refers to a second fluorescent dye which will absorb light energy of a certain wavelength only when associated with proteinaceous material having a certain physical property, will emit light energy of a certain wavelength only when associated with proteinaceous material having a certain physical property, or will absorb light energy of a certain wavelength and emit light energy of a different wavelength only when associated with proteinaceous material having a certain physical property. If a second fluorescent dye associates with non-proteinaceous material or proteinaceous material not having the physical property, then the dye either doesn't absorb light energy and/or doesn't emit light energy, or emits light energy in a manner that a particle analyzer can distinguish between the fluorescence emitted by the second fluorescent dye associated with proteinaceous material having a certain physical property and the fluorescence emitted by the second fluorescent dye associated with non-proteinaceous material or proteinaceous material not having the physical property. Alternatively, the use of a first fluorescent dye in conjunction with a second fluorescent dye will enable the detection and distinction of proteinaceous material having a certain physical property relative to non-proteinaceous material in situations where either the first or the second fluorescent dye associates with non-proteinaceous material in a manner that does not allow a particle analyzer to distinguish these two categories of material.

A physical property of a proteinaceous material is a feature that is present only on a subset of proteinaceous particles present in a sample and includes, without limitation, a structural feature or chemical modification like a post-translational modification. As such, a second fluorescent dye is one that may stain only a subset of proteinaceous particles present in a sample. Non-limiting examples of a structural feature of a proteinaceous material include an α-helical structure, a β-sheet structure, hydrophobicity, and a peptide cleavage. Non-limiting examples of a chemical modification to a proteinaceous material include an acylation, an adenylylation, an alkylation, an amidation, a glycation, a glycosylation, a glypiation, an isoprenylation, a myristoylation, a palimoylation, a pegylation, a phosphorylation, a polysialylation, a prenylation, a sulfation, and an ubiquination.

Detection and distinction of proteinaceous material having a certain physical property based on second fluorescent dye staining may be based on, e.g., changes in fluorescent intensity, changes in the excitation spectrum like peak excitation wavelength, or changes in the emissions spectrum like peak emission wavelength.

In another aspect of this embodiment, the at least one fluorescent dye may include a second fluorescent dye that stains a physical property of non-proteinaceous material in a manner that distinguishes a non-proteinaceous material having the physical property from a non-proteinaceous material not having the physical property. As used herein, the term "stains" when used in reference to a second fluorescent dye a physical property of non-proteinaceous material refers to a second fluorescent dye which will absorb light energy of a certain wavelength only when associated with non-proteinaceous material having a certain physical property, will emit light energy of a certain wavelength only when associated with non-proteinaceous material having a certain physical property, or will absorb light energy of a certain wavelength and emit light energy of a different wavelength only when associated with non-proteinaceous material having a certain physical property. If a second fluorescent dye associates with proteinaceous material or non-proteinaceous material not having the physical property, then the dye either doesn't absorb light energy and/or doesn't emit light energy, or emits light energy in a manner that a particle analyzer can distinguish between the fluorescence emitted by the second fluorescent dye associated with non-proteinaceous material having a certain physical property and the fluorescence emitted by the second fluorescent dye associated with proteinaceous material or non-proteinaceous material not having the physical property. Alternatively, the use of a first fluorescent dye in conjunction with a second fluorescent dye will enable the detection and distinction of non-proteinaceous material having a certain physical property relative to proteinaceous material in situations where either the first or the second fluorescent dye associates with proteinaceous material in a manner that does not allow a particle analyzer to distinguish these two categories of material.

Detection and distinction of non-proteinaceous material having a certain physical property based on second fluorescent dye staining may be based on, e.g., changes in fluorescent intensity, changes in the excitation spectrum like peak excitation wavelength, or changes in the emissions spectrum like peak emission wavelength.

Non-limiting examples of a second fluorescent dye that stains proteinaceous material having a certain physical property and may be used to distinguish proteinaceous particles having a certain physical property from proteinaceous particles not having the certain physical property include 4-(3,6-dimethyl-1,3-benzothiazol-3-ium-2-yl)-N,N-dimethylaniline chloride (Thioflavin T) and its derivates including, e.g., sodium primuline (Thoflavin S) and 4-(1,3-benzothiazol-2-yl)-N-methylaniline (BTA-1); a thiophene and its derivatives based fluorescent oligomers and polymers, described in, e.g., Peter, et al, Am. J. Pathol. 176: 563 (2010) which is hereby incorporated by reference in its entirety; Coumarin and its derivatives including, e.g., 3,3'-methanediylbis(4-hydroxy-2H-chromen-2-one) (Hydroxycoumarin), 11-oxo-2,3,6,7-tetrahydro-1H,5H,11H-pyrano[2,3-f]pyrido[3,2,1-ij]quinoline-10-carboxylic acid (Coumarin 343), and 9-methyl-2,3,6,7-tetrahydro-1H,5H,11H-pyrano[2,3-f]pyrido[3,2,1-ij]quinolin-11-one (Coumarin 102); 2,3,6,7-tetrahydro-1H,5H-benzo[ij]quinolizine and its derivates such as, e.g., (2E)-2-(2,3,6,7-tetrahydro-1H,5H-pyrido[3,2,1-ij]quinolin-9-ylmethylidene)hydrazinecarbothioamide, 9-[(E)-phenyldiazenyl]-2,3,6,7-tetrahydro-1H,5H-pyrido[3,2,1-ij]quinoline, (2,3,6,7-tetrahydro-1H,5H-pyrido[3,2,1-ij]quinolin-9-ylmethylidene) propanedinitrile, 9-(2,2-Dicyanovinyl)julolidine (DCVJ), and (2E)-2-cyano-3-(2,3,6,7-tetrahydro-1H,5H-pyrido[3,2,1-ij]quinolin-9-yl)prop-2-enoic acid (CCVJ), 9-(diethylamino)-5H-benzo[a]phenoxazin-5-one (Nile red), 3,3'-([1,1'-biphenyl]-4,4'-diyl)bis(4-aminonaphthalene-1-sulfonic acid) (Congo red) and its derivatives such as, e.g., [(trans,trans)-1-bromo-2,5-bis-(3-hydroxycarbonyl-4-hydroxy)styrylbenzene] (BSB) 4-[(E)-2-[2-bromo-4-[(E)-2-(4-hydroxyphenyl)vinyl]phenyl]vinyl]phenol (K114), 8-(phenylamino)naphthalene-1-sulfonic acid (ANS) and its derivatives such as, e.g., dipotassium 4,4'-bis(phenylamino)-1,1'-binaphthalene-5,5'-disulfonate (Bis-ANS); benzenesulfonic acid sodium salt and its derivatives including, e.g., 3-(4-anilinophenylazo)benzenesulfonic acid sodium salt (Orange IV), 1,6-Diphenyl-1,3,5-hexatriene (DPH) and its derivatives like 1-(4-trimethylammoniumphenyl)-6-phenyl-1,3,5-hexatriene p-toluenesulfonate (TMA-DPH); and 4',6-diamidino-2-phenylindole dihydrochloride (DAPI). The peak excitation and emission wavelengths for fluorescent dyes useful as a second fluorescent dye disclosed herein are listed in Table 3. Other fluorescent dyes useful as a second fluorescent dye disclosed herein are known by a person skilled in the art.

TABLE 3

Fluorescent Dye Peak Excitation and Emission Wavelengths[a]

| Fluorescent Dye | Peak Excitation λ (nm) | Peak Emission λ (nm) |
| --- | --- | --- |
| Thioflavin T | 440 | 480 |
| Thoflavin S | 440 | 480 |
| 4-(1,3-benzothiazol-2-yl)-N-methylaniline (BTA-1) | 440 | 480 |
| Coumarin | 384 | 470 |
| Hydroxycoumarin | 387 | 448 |
| Coumarin 343 | 445 | 492 |
| Coumarin 102 | 389 | 465 |
| 2,3,6,7-Tetrahydro-1H,5H-benzo[ij]quinolizine | | |
| (2E)-2-(2,3,6,7-tetrahydro-1H,5H-pyrido[3,2,1-ij]quinolin-9-ylmethylidene)hydrazinecarbothioamide | 450 | 510 |
| 9-[(E)-phenyldiazenyl]-2,3,6,7-tetrahydro-1H,5H-pyrido[3,2,1-ij]quinoline | 450 | 510 |
| DCVJ | 456 | 493 |
| (2E)-2-cyano-3-(2,3,6,7-tetrahydro-1H,5H-pyrido[3,2,1-ij]quinolin-9-yl)prop-2-enoic acid (CCVJ) | 450 | 500 |
| Nile red | 552 | 636 |
| Congo red | 497 | 630 |
| BSB | 340 | 520 |
| 4-[(E)-2-[2-bromo-4-[(E)-2-(4-hydroxyphenyl)vinyl]phenyl]vinyl]phenol (K114) | 450 | 620 |
| ANS | 372 | 480 |
| Bis-ANS | 395 | 500 |
| benzenesulfonic acid sodium salt | 354 | 390 |
| 3-(4-Anilinophenylazo)benzenesulfonic acid sodium salt (Orange IV) | 350 | 460 |
| DPH | 350 | 452 |
| TMA-DPH | 350 | 452 |
| 4',6-Diamidino-2-phenylindole dihydrochloride (DAPI) | 358 | 461 |

[a]Indicated values of excitation and emission maximum are average values, but a person of skill understands that these values can vary depending on conditions, such as, e.g., solution pH, ionic strength, dye concentration and/or dye conformation.

The sample may comprise a counting standard. A counting standard comprising a calibrated suspension of particles of known amount or concentration. A counting standard is used to define a number of particles in a sample and will allow for the determination of the number of subvisible particles present in a sample. Particles may be of any regular (geometric) or irregular shape, may be made from any material, and may be fluorescent or non-fluorescent. For absolute counts, a specific volume of the counting standard is added to a specific volume of sample, so that the ratio of sample volume to a counting standard volume is known. The volume of sample analyzed can be calculated from the number of counting standard particle events, and can be used with sample particle events to determine concentration. In general, at least 1,000 counting standard particle events should be acquired to assure a statistically significant determination of sample volume. In aspects of this embodiment, a method disclosed herein may count, e.g., at least 1,000, at least 2,000, at least 3,000, at least 4,000, at least 5,000, at least 6,000, at least 7,000, at least 8,000, at least 9,000, or at least 10,000 counting standard particle events.

A fluorescent counting standard includes particles that may fluorescent across a wide range of excitation and emission wavelengths. For example, a fluorescent counting standard disclosed herein encompass particles which can emit in a variety of spectra, including ultraviolet, visible (including violet, blue, cyan, green, yellow, orange, and red), near infrared, medium infrared, and far infrared.

Particles from a fluorescent counting standard useful to practice the methods disclosed herein may exhibit an excitation spectrum in the ultraviolet, visible, near infrared, medium infrared, or far infrared spectrums. In an aspect of this embodiment, particles from a fluorescent counting standard useful to practice the methods disclosed herein may exhibit an excitation spectrum within the range of about 300 nm to about 800 nm. In an aspect of this embodiment, particles from a fluorescent counting standard useful to practice the methods disclosed herein may exhibit an excitation spectrum within the range of about 300 nm to about 635 nm. In aspects of this embodiment, particles from a fluorescent counting standard useful to practice the methods disclosed herein may exhibit an excitation spectrum in the range of about 300 nm to about 350 nm, about 350 nm to about 380 nm, about 380 nm to about 450 nm, about 420 nm to about 460 nm, about 450 nm to about 495 nm, about 460 nm to about 500 nm, about 495 nm to about 570 nm, about 500 nm to about 520 nm, about 520 nm to about 550 nm, about 550 nm to about 740 nm, about 570 nm to about 590 nm, about 590 nm to about 620 nm, about 620 nm to about 750 nm, or about 750 nm to about 800 nm. In yet other aspects of this embodiment, particles from a fluorescent counting standard useful to practice the methods disclosed herein may exhibit an peak excitation wavelength in the range of about 300 nm to about 350 nm, about 350 nm to about 380 nm, about 380 nm to about 450 nm, about 420 nm to about 460 nm, about 450 nm to about 495 nm, about 460 nm to about 500 nm, about 495 nm to about 570 nm, about 500 nm to about 520 nm, about 520 nm to about 550 nm, about 550 nm to about 740 nm, about 570 nm to about 590 nm, about 590 nm to about 620 nm, about 620 nm to about 750 nm, or about 750 nm to about 800 nm. In still other aspects of this embodiment, particles from a fluorescent counting standard useful to practice the methods disclosed herein may exhibit an peak excitation wavelength of about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, or about 630 nm.

Particles from a fluorescent counting standard useful to practice the methods disclosed herein may exhibit an emissions spectrum in the ultraviolet, visible, near infrared, medium infrared, or far infrared spectrums. In an aspect of this embodiment, particles from a fluorescent counting standard useful to practice the methods disclosed herein may exhibit an emission spectrum within the range of about 300 nm to about 800 nm. In an aspect of this embodiment, particles from a fluorescent counting standard useful to practice the methods disclosed herein may exhibit an emission spectrum within the range of about 385 nm to about 800 nm. In aspects of this embodiment, particles from a fluorescent counting standard useful to practice the methods disclosed herein may exhibit an emission spectrum in the range of about 300 nm to about 350 nm, about 350 nm to about 380 nm, about 380 nm to about 450 nm, about 420 nm to about 460 nm, about 450 nm to about 495 nm, about 460 nm to about 500 nm, about 495 nm to about 570 nm, about 500 nm to about 520 nm, about 520 nm to about 550 nm, about 550 nm to about 740 nm, about 570 nm to about 590 nm, about 590 nm to about 620 nm, about 620 nm to about 750 nm, or about 750 nm to about 800 nm. In yet other aspects of this embodiment, particles from a fluorescent counting standard useful to practice the methods disclosed herein may exhibit an peak emission wavelength in the range of about 300 nm to about 350 nm, about 350 nm to about 380 nm, about 380 nm to about 450 nm, about 420 nm to about 460 nm, about 450 nm to about 495 nm, about 460 nm to about 500 nm, about 495 nm to about 570 nm, about 500 nm to about 520 nm, about 520 nm to about 550 nm, about 550 nm to about 740 nm, about 570 nm to about 590 nm, about 590 nm to about 620 nm, about 620 nm to about 750 nm, or about 750 nm to about 800 nm. In still other aspects of this embodiment, particles from a fluorescent counting standard useful to practice the methods disclosed herein may exhibit an peak emission wavelength of about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, about 630 nm, about 640 nm, about 650 nm, about 660 nm, about 670 nm, about 680 nm, about 690 nm, about 700 nm, about 710 nm, about 720 nm, about 730 nm, about 740 nm, about 750 nm, about 760 nm, about 770 nm, about 780 nm, about 790 nm, or about 800 nm.

Non-limiting examples of a counting standard include COUNTBRIGHT™ Absolute Counting Beads (Invitrogen Corp., Carlsbad, CA), CYTO-CAL™ Count Control (Thermo Fisher Scientific Inc., Waltham, MA), FLOW CYTOMETRY ABSOLUTE COUNT STANDARD™ (Bangs Laboratories, Inc., Fishers, IN), PERFECT-COUNT™ Microspheres (Cytognos, S.L., Salmanca), and SPHERO™ AccuCount Particles (Spherotech, Inc., Lake Forest, IL)

The present specification discloses, in part, collecting data from at least one light scatter parameter. A "parameter" is synonymous with "independent variable" and refers to any of the simultaneous, independent measurements obtained from particles or cells being analyzed in a particle analyzer. The combination of two or more parameters, by some mathematical function, is defined as yielding another parameter. A LS parameter refers to a light scatter signal measured without specifying any particular angle or angular range. Light scatter parameters include FLS, Side Angle Light Scatter (SALS), and Reverse Angle Light Scatter (RALS). FLS refers to a light scatter signal measured in an angle range of between greater than 0° and less than 90° from the axis of the incident light in the forward direction. SALS, also known as Orthogonal Light Scatter (OLS) or High Angle Light Scatter (HALS), refers to a light scatter signal measured at or about 90° from the incident light axis, in the forward direction. RALS refers to a light scatter signal measured in an angle range of about 160°-176° from the incident light axis, i.e., in a reverse direction relative to the forward direction of incident light.

FLS can be subdivided into Low Angle Light Scatter (LALS), Median Angle Light Scatter (MALS), which includes Low Median Angle Light Scatter (LMALS) and Upper Median Angle Light Scatter (UMALS). Low Angle Light Scatter (LALS) refers to a light scatter signal measured in an angle range of more than 0° and less than 9° from the axis of the incident light. In aspects of this embodiment, LALS is measured in an angle range of about 3° to about 7° from the axis of the incident light, in the forward direction, or about 5.1° from the axis of the incident light, in the forward direction.

Median Angle Light Scatter (MALS) refers to a light scatter signal measured in an angle range of between 9° and 70° from the incident light axis. Low Median Angle Light Scatter (LMALS) refers to a subset of MALS, where a light scatter signal is measured in an angle range of about 9° to about 20° from the incident light axis. Upper Median Angle Light Scatter (UMALS) refers to a subset of MALS, where a light scatter signal is measured in an angle range of about 20° to about 70° from the incident light axis, in the forward direction. In aspects of this embodiment, UMALS is measured in an angle range of about 20° to about 65° from the incident light axis, in the forward direction, or angle range of about 20° to about 42° from the incident light axis, in the forward direction.

Data collected from at least one light scatter parameter defines a particle's size. In an aspect of this embodiment, the data collected from the at least one light scatter parameter may represent a particle size based upon particles present in size standard as disclosed herein. In another aspect of this embodiment, the data collected from the at least one light scatter parameter may represent a particle size based upon the particles present in a test sample. In other aspects of this embodiment, the data collected may represent particles having a size of, e.g., less than or equal to 0.1 µm, less than or equal to 0.5 µm, less than or equal to 0.75 µm, less than or equal to 1 µm, less than or equal to 2.5 µm, less than or equal to 5 µm, less than or equal to 7.5 µm, less than or equal to 10 µm, less than or equal to 25 µm, less than or equal to 50 µm, less than or equal to 75 µms, less than or equal to 100 µm, less than or equal to 150 µm, less than or equal to 175 µm, less than or equal to 200 µm, less than or equal to 225 µm, less than or equal to 250 µm, less than or equal to 275 µm, or less than or equal to 300 µm. In other aspects of this embodiment, the data collected may represent particles having a size between, e.g., about 0.05 µm to about 200 µm, about 0.05 µm to about 150 µm, about 0.05 µm to about 100 µm, about 0.05 µm to about 75 µm, about 0.05 µm to about 50 µm, about 0.05 µm to about 20 µm, about 0.1 µm to about 200 µm, about 0.1 µm to about 150 µm, about 0.1 µm to about 100 µm, about 0.1 µm to about 75 µm, about 0.1 µm to about 50 µm, or about 0.1 µm to about 20 µm.

The present specification discloses, in part, collecting data from at least one light loss parameter. When the beam of incident light strikes a particle, the light is either scattered or absorbed, both of which remove energy from the incident light and the incident beam is attenuated. This attenuation is referred to as extinction. A Light Loss (LL) parameter refers to the amount of light energy absorbed (loss). Axial Light Loss (ALL), also known as forward extinction or AL2, refers to the decrease in light energy due to a particle passing through a beam of incident light and being detected by a photo-detector.

The present specification discloses, in part, collecting data from at least one fluorescence parameter. Data from at least one fluorescence parameter is collected as a fluorescence intensity, or the amount of photons emitted from the fluorophoric particle after excitation. Data collected from a fluorescence parameter may represent the presence of a proteinaceous material based upon fluorescence intensity emitted from the first fluorescent dye disclosed herein, may represent the presence of a proteinaceous material having the physical property based upon fluorescence intensity emitted from the second fluorescent dye disclosed herein, and/or may represent the particle number based upon fluorescence intensity emitted from the fluorescent counting standard disclosed herein.

In an aspect of this embodiment, the data collected from the at least one fluorescence parameter may include a first fluorescence parameter representing presence of a proteinaceous material based upon fluorescence intensity emitted from the first fluorescent dye.

In another aspect of this embodiment, the data collected from the at least one fluorescence parameter may include a first fluorescence parameter representing presence of a non-proteinaceous material based upon fluorescence intensity emitted from the first fluorescent dye.

In yet another aspect of this embodiment, the data collected from the at least one fluorescence parameter may include a first fluorescence parameter representing presence of a proteinaceous material based upon fluorescence intensity emitted from the first fluorescent dye, and a second fluorescence parameter representing particle number based upon fluorescence intensity emitted from the fluorescent counting standard.

In still another aspect of this embodiment, the data collected from the at least one fluorescence parameter may include a first fluorescence parameter representing presence of a non-proteinaceous material based upon fluorescence intensity emitted from the first fluorescent dye, and a second fluorescence parameter representing particle number based upon fluorescence intensity emitted from the fluorescent counting standard.

In another aspect of this embodiment, the data collected from the at least one fluorescence parameter may include a first fluorescence parameter representing presence of a proteinaceous material based upon fluorescence intensity emitted from the first fluorescent dye, a second fluorescence parameter representing particle number based upon fluorescence intensity emitted from the fluorescent counting standard, and a third fluorescence parameter representing presence of a proteinaceous material having a certain physical property based upon fluorescence intensity emitted from the second fluorescent dye.

In yet another aspect of this embodiment, the data collected from the at least one fluorescence parameter may include a first fluorescence parameter representing presence of a non-proteinaceous material based upon fluorescence intensity emitted from the first fluorescent dye, a second fluorescence parameter representing particle number based upon fluorescence intensity emitted from the fluorescent counting standard, and a third fluorescence parameter representing presence of a non-proteinaceous material having a certain physical property based upon fluorescence intensity emitted from the second fluorescent dye.

Aspects of the present specification disclose, in part, collecting data that is not an electrical sensing parameter. Examples of an electrical parameter can be Direct Current (DC) impedance, Radio Frequency (RF) conductivity, and Opacity (OP). DC impedance and RF conductivity are electronic sensing parameters which refer to the Coulter Principle of aperture impedance cell sensing. DC impedance refers to the pulse peak information obtained from applying a direct or low-frequency current. The peak amplitude of the DC pulse is a function of particle volume and occurs when no current flows through the particle. RF conductivity refers to the pulse peak information derived from the measurement obtained from applying a high-frequency current. RF is a function of cell volume and internal conductivity and occurs when current flows through the particle. OP refers to the signal value or data obtained by the division of a RF conductivity signal by a DC impedance signal. Opacity is an electrical sensing parameter which is independent of size, but is a function of internal conductivity. In an embodiment, data collected from a particle is not an electrical sensing parameter. In an aspect of this embodiment, data collected from a particle is not a DC impedance signal. In another aspect of this embodiment, data collected from a particle is not a RF conductivity signal. In yet another aspect of this embodiment, data collected from a particle is not an OP signal.

The present specification discloses, in part, analyzing the data to characterize the population of subvisible particles in the sample. Collected data are stored as computer files. For example, data corresponding to a sample can be stored as a listmode file and/or histogram file. A listmode file contains a complete listing of all events corresponding to all the parameters collected, as specified by a user-defined acquisition protocol. Once data has been collected and written into a listmode file the data can be replayed using the same or different acquisition protocol or other program designed for analysis of flow cytometry data. For example, an acquisition protocol may be adjusted in order to define which region, gate, or parameter should be analyzed and displayed.

For example, collected data may be analyzed to define particle size and presence of proteinaceous material in order to determine size and presence of proteinaceous subvisible particles. This is typically done by employing the gating database established by a size standard to set gates of defined size ranges which are used to estimate the size of each particle in the test sample and collect data regarding size distribution of all particles in the test sample. One the size distribution of the particles is determined, this data may be gated based on size and the resulting subset of sized particles analyzed for the presence of proteinaceaous material. In this manner, data regarding the size and presence of proteinaceous subvisible particles in a sample can be determined. Such data may be graphically displayed as a one-parameter histogram. Once determined this data may be compared to total number of particles in order to define other useful characterizations including, e.g., the size and presence of non-proteinaceous subvisible particles and/or the presence of visible particles. For example, to qualitatively determine the presence of sized non-proteinaceous subvisible particles the presence value of all sized subvisible particles is subtracted by the presence value of sized proteinaceous subvisible particles. Similarly, data regarding the size and presence of non-proteinaceous subvisible particles in a sample can be determined as described above except that resulting subset of sized particles is analyzed for the presence of non-proteinaceous material.

The data representing size and presence of proteinaceous subvisible particles in a sample may be further analyzed to define particle number in order to determine the absolute number of the sized proteinaceous subvisible particles. This may be accomplished by gating the data representing particle size and the resulting subset of sized particles analyzed for particle number and the presence of proteinaceaous material. In this manner, data regarding the absolute number and size of proteinaceous subvisible particles in a sample can be determined. Such data may be graphically displayed as a two-parameter histogram. Once determined this data may be compared to total number of particles in order to define other useful characterizations including, e.g., the number, size and presence of non-proteinaceous subvisible particles and/or the number and presence of visible particles. For example, to determine the absolute number of sized non-proteinaceous subvisible particles the absolute number of all sized subvisible particles is subtracted by the absolute number of sized proteinaceous subvisible particles. Similarly, data regarding absolute number of the sized non-proteinaceous subvisible particles in a sample can be determined as described above except that resulting subset of sized particles is analyzed for particle number and the presence of non-proteinaceaous material.

The data representing absolute number, size and presence of proteinaceous subvisible particles in a sample may be further analyzed to determine whether proteinaceous subvisible particles, or a subset thereof, have a certain physical property in order to determine the fraction of counted, sized proteinaceous subvisible particles with and without the physical property. This may be accomplished by gating the data representing particle size and the resulting subset of sized particles analyzed for particle number and the presence of proteinaceaous material with or without the physical property. In this manner, data regarding the absolute number and size of proteinaceous subvisible particles with and without a certain physical property in a sample can be determined. Such data may be graphically displayed as a two-parameter histogram. Similarly, data regarding whether non-proteinaceous subvisible particles, or a subset thereof, have a certain physical property in order to determine the fraction of counted, sized non-proteinaceous subvisible particles with and without the physical property can be determined as described above except that the resulting subset of sized particles is analyzed for particle number and the presence of non-proteinaceaous material with or without the physical property.

As another example, collected data may be analyzed to define particle size, particle number, and presence of proteinaceaous material in order to determine absolute number and size of proteinaceous subvisible particles. This is typically done by employing the gating database established by a size standard to set gates of defined size ranges which are used to estimate the size of each particle in the test sample and collect data regarding size distribution of all particles in the test sample. Once the size distribution of the particles is determined, this data may be gated based on size and the resulting subset of sized particles analyzed for particle number and the presence of proteinaceous material. In this manner, data regarding the absolute number and size of proteinaceous subvisible particles in a sample can be determined. Such data may be graphically displayed as a two-parameter histogram. Once determined this data may be compared to the total number of particles in order to define other useful characterizations including, e.g., the number, size and presence of non-proteinaceous subvisible particles and/or the number and presence of visible particles. For example, to determine the absolute number of sized non-proteinaceous subvisible particles, the absolute number of all sized subvisible particles is subtracted by the absolute number of sized proteinaceous subvisible particles. As discussed above, the data representing absolute number, size and presence of proteinaceous subvisible particles in a sample may be further analyzed to determine whether proteinaceous subvisible particles, or a subset thereof, have a certain physical property in order to determine the fraction of counted, sized proteinaceous subvisible particles with and without the physical property. Similarly, data regarding the absolute number and size of non-proteinaceous subvisible particles in a sample can be determined as described above except that the resulting subset of sized particles is analyzed for particle number and the presence of non-proteinaceous material.

As another example, collected data may be analyzed to define particle size, particle number, presence of proteinaceous material, and presence of a certain physical property in order to determine absolute number and size of proteinaceous subvisible particles with and without the physical property. This is typically done by employing the gating database established by a size standard to set gates of defined size ranges which are used to estimate the size of each particle in the test sample and collect data regarding size distribution of all particles in the test sample. One the size distribution of the particles is determined, this data may be gated based on size and the resulting subset of sized particles analyzed for particle number and the presence of proteinaceous material with or without the physical property. In this manner, data regarding the absolute number and size of proteinaceous subvisible particles with and without a certain physical property in a sample can be determined. Such data may be graphically displayed as a two-parameter histogram. Similarly, data regarding the absolute number and size of non-proteinaceous subvisible particles with and without a certain physical property in a sample can be determined as described above except that the resulting subset of sized particles analyzed for particle number and the presence of non-proteinaceous material with or without the physical property.

Thus, in one aspect of this embodiment, the data may be analyzed to define the particle size and presence of the proteinaceous material to determine size and presence of proteinaceous subvisible particles, thereby characterizing the population of subvisible particles in the sample. In another aspect of this embodiment, the data may be analyzed to define the particle size, the particle number, and presence of the proteinaceous material to determine absolute number and size of proteinaceous subvisible particles, thereby characterizing the population of subvisible particles in the sample. In yet another aspect of this embodiment, the data may be analyzed to define the particle size, the particle number, presence of the proteinaceous material, and presence of the physical property to determine absolute number and size of proteinaceous subvisible particles with and without the physical property, thereby characterizing the population of subvisible particles in the sample. In still another aspect of this embodiment, the data may be analyzed to determine absolute number of sized non-proteinaceous subvisible particles by subtracting the absolute number of all sized subvisible particles by the absolute number of sized proteinaceous subvisible particles.

In another aspect of this embodiment, the data may be analyzed to define the particle size and presence of the non-proteinaceous material to determine size and presence of non-proteinaceous subvisible particles, thereby characterizing the population of subvisible particles in the sample. In another aspect of this embodiment, the data may be analyzed to define the particle size, the particle number, and presence of the non-proteinaceous material to determine absolute number and size of non-proteinaceous subvisible particles, thereby characterizing the population of subvisible particles in the sample. In yet another aspect of this embodiment, the data may be analyzed to define the particle size, the particle number, presence of the non-proteinaceous material, and presence of the physical property to determine absolute number and size of non-proteinaceous subvisible particles with and without the physical property, thereby characterizing the population of subvisible particles in the sample. In still another aspect of this embodiment, the data may be analyzed to determine absolute number of sized proteinaceous subvisible particles by subtracting the absolute number of all sized subvisible particles by the absolute number of sized non-proteinaceous subvisible particles.

Aspects of the present specification can also be described as follows:

1. A method of characterizing a population of subvisible particles in a sample, the method comprising the steps of: a) calibrating a particle analyzer using a size standard; b) interrogating the sample as the sample passes through a sensing zone of the particle analyzer, the sample comprising a fluorescent counting standard and at least one fluorescent dye, wherein the interrogation includes one or more wavelengths that can interrogate the size standard, interrogate or excite the fluorescent counting standard, and interrogate or excite the at least one fluorescent dye, and wherein the at least one fluorescent dye includes a first fluorescent dye that stains a proteinaceous material in a manner that distinguishes the proteinaceous material from a non-proteinaceous material, and a second fluorescent dye that stains a physical property of the proteinaceous material in a manner that distinguishes a proteinaceous material having the physical property from a proteinaceous material not having the physical property; c) collecting data from at least one light scatter parameter and at least one fluorescence parameter, wherein the data collected from the at least one light scatter parameter represents a particle size based upon the size standard calibration, and wherein the data collected from the at least one fluorescence parameter includes a first fluorescence parameter representing presence of a proteinaceous material based upon fluorescence intensity emitted from the first fluorescent dye, a second fluorescence parameter representing a particle number based upon fluorescence intensity emitted from the fluorescent counting standard, and a third fluorescence parameter representing presence of a proteinaceous material having the physical property based upon fluorescence intensity emitted from the second fluorescent dye; and d) analyzing the data to define the particle size, the particle number, presence of the proteinaceous material, and presence of the physical property in order to determine an absolute number and size of proteinaceous subvisible particles with and without the physical property, thereby characterizing the population of subvisible particles in the sample.

2. A method of characterizing a population of subvisible particles in a sample, the method comprising the steps of: a) calibrating a particle analyzer using a size standard; b) interrogating the sample as the sample passes through a sensing zone of the particle analyzer, the sample comprising a fluorescent counting standard and at least one fluorescent dye, wherein the interrogation includes one or more wavelengths that can interrogate the size standard, interrogate or excite the fluorescent counting standard, and interrogate or excite the at least one fluorescent dye, and wherein the at least one fluorescent dye includes a first fluorescent dye that stains a proteinaceous material in a manner that distinguishes the proteinaceous material from a non-proteinaceous material; c) collecting data from at least one light scatter parameter and at least one fluorescence parameter, wherein the data collected from the at least one light scatter parameter represents a particle size based upon the size standard calibration, and wherein the data collected from the at least one fluorescence parameter includes a first fluorescence parameter representing presence of the proteinaceous material based upon fluorescence intensity emitted from the first fluorescent dye, and a second fluorescence parameter representing a particle number based upon fluorescence intensity emitted from the fluorescent counting standard; and d) analyzing the data to define the particle size, the particle number, and presence of the proteinaceous material in order to determine an absolute number and size of proteinaceous subvisible particles, thereby characterizing the population of subvisible particles in the sample.

3. The method of embodiment 2, wherein the data analysis step further comprises determining an absolute number of sized non-proteinaceous subvisible particles by subtracting an absolute number of all sized subvisible particles by the absolute number of sized proteinaceous subvisible particles.

4. The method of embodiment 2 or 3, wherein in the interrogating the sample step: the at least one fluorescent dye includes a second fluorescent dye that stains a physical property of the proteinaceous material in a manner that distinguishes a proteinaceous material having the physical property from a proteinaceous material not having the physical property, and the interrogation includes one or more wavelengths that can excite the second fluorescent dye; in the collection data step: collecting data further includes collecting data from a third fluorescence parameter, the third fluorescence parameter representing presence of the proteinaceous material having the physical property based upon fluorescence intensity emitted from the second fluorescent dye; and in the data analysis step: analyzing the data to define presence of the physical property in order to determine a fraction of counted, sized proteinaceous subvisible particles with or without the physical property, thereby characterizing the population of subvisible particles in the sample.

5. A method of characterizing a population of subvisible particles in a sample, the method comprising the steps of: a) calibrating a particle analyzer using a size standard; b) interrogating the sample as the sample passes through a sensing zone of the particle analyzer, the sample comprising at least one fluorescent dye, wherein the interrogation includes one or more wavelengths that can interrogate the size standard, and excite the at least one fluorescent dye, and wherein the at least one fluorescent dye includes a first fluorescent dye that stains a proteinaceous material in a manner that distinguishes the proteinaceous material from a non-proteinaceous material; c) collecting data from at least one light scatter parameter and at least one fluorescence parameter, wherein the data collected from the at least one light scatter parameter represents a particle size based upon the size standard calibration, and wherein the data collected from the at least one fluorescence parameter includes a first fluorescence parameter representing presence of the proteinaceous material based upon fluorescence intensity emitted from the first fluorescent dye; and d) analyzing the data to define the particle size and presence of the proteinaceous material in order to determine a size and presence of proteinaceous subvisible particles, thereby characterizing the population of subvisible particles in the sample.

6. The method of embodiments 1-5, wherein the size standard comprises particles having mean diameters of 0.5 µm, 1.0 µm, 2.0 µm, 4.5 µm, 6.0 µm, 10 µm, or a combination thereof.

7. The method of embodiments 1-6, wherein the first fluorescent dye has a peak fluorescence excitation wavelength from between about 300 nm to about 635 nm.

8. The method of embodiments 1-7, wherein the first fluorescent dye has a peak fluorescence emission wavelength from between about 350 nm to about 800 nm.

9. The method of embodiments 1-8, wherein the first fluorescent dye has a peak fluorescence excitation wavelength of about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, or about 630 nm.

10. The method of embodiments 1-9, wherein the first fluorescent dye has a peak fluorescence emission wavelength of about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, about 630 nm, about 640 nm, about 650 nm, about 660 nm, about 670 nm, about 680 nm, about 690 nm, about 700 nm, about 710 nm, about 720 nm, about 730 nm, about 740 nm, about 750 nm, about 760 nm, about 770 nm, about 780 nm, about 790 nm, or about 800 nm.

11. The method of embodiments 1-10, wherein the first fluorescent dye is a styryl dye, a merocyanine dye, 3-(2-benzothiazolyl-7-(diethylamino)-coumarin (BTDEC), 3-(2-benzimidazolyl)-7-(diethylamino)-coumarin (BIDEC), 3-(2-benzimidazolyl)-7-coumarin (BIC), 3-(2-benzimidazolyl)-7-(dipropylamino)-coumarin (BIDPC), 3-(2-benzoxazolyl)-7-(diethylamino)-coumarin (BODEC), 3-(6-methyl-2-benzoxazolyl)-7-(diethylamino)-coumarin (MBODEC), 3-(diethylamino)-7-imino-7H-(1)benzopyrano (3',2':3,4)pyrido(1,2-a)benzimidazole-6-carbonitrile (DIBPBC), 3-(diethylamino)-7-oxo-7H-(1)

benzopyrano(3',2':3,4) (DOBPBC), dipyrromethenboron difluoride, a photoluminescent metal complex, or a hydroxyquinolone.

12. The method of embodiments 5-11, wherein in the interrogating the sample step: the sample further comprises a fluorescent counting standard, and the interrogation includes one or more wavelengths that can interrogate or excite the fluorescent counting standard; and in the collection data step: the at least one fluorescence parameter includes a second fluorescence parameter representing a particle number based upon fluorescence intensity emitted from the fluorescent counting standard; in the data analysis step: analyzing the data to define the particle number in order to determine an absolute number of the sized proteinaceous subvisible particles, thereby characterizing the population of subvisible particles in the sample.

13. The method of embodiments 1-4 or 12, wherein the fluorescent counting standard comprises particles having a peak fluorescence excitation wavelength from between about 300 nm to about 635 nm.

14. The method of embodiments 1-4, 12, or 13, wherein the fluorescent counting standard comprises particles having a peak fluorescence emission wavelength from between about 385 nm and about 800 nm.

15. The method of embodiments 12-14, wherein the data analysis step further comprises determining absolute number of sized non-proteinaceous subvisible particles by subtracting the absolute number of all sized subvisible particles by the absolute number of sized proteinaceous subvisible particles.

16. The method of embodiments 12-15, wherein in the interrogating the sample step: the at least one fluorescent dye includes a second fluorescent dye that stains a physical property of the proteinaceous material in a manner that distinguishes a proteinaceous material having the physical property from a proteinaceous material not having the physical property, and the interrogation includes one or more wavelengths that can excite the second fluorescent dye; and in the collection data step: collecting data further includes collecting data from a third fluorescence parameter, the third fluorescence parameter representing presence of the proteinaceous material having the physical property based upon fluorescence intensity emitted from the second fluorescent dye; in the data analysis step: analyzing the data to define presence of the physical property in order to determine the fraction of counted, sized proteinaceous subvisible particles with or without the physical property, thereby characterizing the population of subvisible particles in the sample.

17. The method of embodiments 1, 4, or 16, wherein the physical property is a structural feature or chemical modification.

18. The method of embodiment 17, wherein the structural feature is an α-helical structure, a β-sheet structure, or a peptide cleavage.

19. The method of embodiment 17, wherein the chemical modification is an acylation, an adenylylation, an alkylation, an amidation, a glycation, a glycosylation, a glypiation, an isoprenylation, a myristoylation, a palmoylation, a pegylation, a phosphorylation, a prenylation, a sulfation, or an ubiquination.

20. The method of embodiments 1, 4, or 16-19, wherein the second fluorescent dye has a peak fluorescence excitation wavelength from between about 350 nm to about 635 nm.

21. The method of embodiments 1, 4, or 16-20, wherein the second fluorescent dye has a peak fluorescence emission wavelength from between about 350 nm to about 800 nm.

22. The method of embodiments 1, 4, or 16-21, wherein the second fluorescent dye has a peak fluorescence excitation wavelength of about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, or about 630 nm.

23. The method of embodiments 1, 4, or 16-22, wherein the second fluorescent dye has a peak fluorescence emission wavelength of about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, about 630 nm, about 640 nm, about 650 nm, about 660 nm, about 670 nm, about 680 nm, about 690 nm, about 700 nm, about 710 nm, about 720 nm, about 730 nm, about 740 nm, about 750 nm, about 760 nm, about 770 nm, about 780 nm, about 790 nm, or about 800 nm.

24. The method of embodiments 1, 4, or 16-23, wherein the second fluorescent dye is 4-(3,6-dimethyl-1,3-benzothiazol-3-ium-2-yl)-N,N-dimethylaniline chloride (Thioflavin T), sodium primuline (Thoflavin S), 4-(1,3-benzothiazol-2-yl)-N-methylaniline (BTA-1), a thiophene-based oligomeric and polymeric dye, Coumarin, 3,3'-methanediylbis(4-hydroxy-2H-chromen-2-one) (hydroxycoumarin), 11-oxo-2,3,6,7-tetrahydro-1H,5H,11H-pyrano[2,3-f]pyrido[3,2,1-ij]quinoline-10-carboxylic acid (Coumarin 343), 9-methyl-2,3,6,7-tetrahydro-1H,5H,11H-pyrano[2,3-f]pyrido[3,2,1-ij]quinolin-11-one (Coumarin 102), 2,3,6,7-tetrahydro-1H,5H-benzo[ij]quinolizine, (2E)-2-(2,3,6,7-tetrahydro-1H,5H-pyrido[3,2,1-ij]quinolin-9-ylmethylidene)hydrazinecarbothioamide, 9-[(E)-phenyldiazenyl]-2,3,6,7-tetrahydro-1H,5H-pyrido[3,2,1-ij]quinoline, (2,3,6,7-tetrahydro-1H,5H-pyrido[3,2,1-ij]quinolin-9-ylmethylidene) propanedinitrile, 9-(2,2-Dicyanovinyl)julolidine (DCVJ), (2E)-2-cyano-3-(2,3,6,7-tetrahydro-1H,5H-pyrido[3,2,1-ij]quinolin-9-yl) prop-2-enoic acid (CCVJ), 9-(diethylamino)-5H-benzo[a]phenoxazin-5-one (Nile red), 3,3'-([1,1'-biphenyl]-4,4'-diyl)bis(4-aminonaphthalene-1-sulfonic acid) (Congo red), [(trans,trans)-1-bromo-2,5-bis-(3-hydroxycarbonyl-4-hydroxy)styrylbenzene] (BSB), 4-[(E)-2-[2-bromo-4-[(E)-2-(4-hydroxyphenyl) vinyl]phenyl]vinyl]phenol (K114), 8-(phenylamino)naphthalene-1-sulfonic acid (ANS), dipotassium 4,4'-bis(phenylamino)-1,1'-binaphthalene-5,5'-disulfonate (Bis-ANS), benzenesulfonic acid sodium salt, 3-(4-anilinophenylazo)benzenesulfonic acid sodium salt (Orange IV), 1,6-Diphenyl-1,3,5-hexatriene (DPH), 1-(4-trimethylammoniumphenyl)-6-phenyl-1,3,5-hexatriene p-toluenesulfonate (TMA-DPH), or 4',6-diamidino-2-phenylindole dihydrochloride (DAPI).

25. The method of embodiments 1-25, wherein the sample is a pharmaceutical preparation.
26. The method of embodiment 25, wherein the pharmaceutical preparation comprises a proteinaceous material that is a pharmaceutical active ingredient, an adjuvant, or an excipient.
27. The method of embodiment 26, wherein the pharmaceutical active ingredient is a blood protein.
28. The method of embodiment 26, wherein the pharmaceutical active ingredient is a blood coagulation protein.
29. The method of embodiment 26, wherein the pharmaceutical active ingredient is ADAMTS-13, α1-antiplasmin, α2-antiplasmin, antithrombin, antithrombin III, cancer procoagulant, erythropoietin, Factor II, Factor IIa, Factor V, Factor Va, Factor VI, Factor VIa, Factor VII, Factor VIIa, Factor VIII, Factor VIIIa, Factor IX, Factor IXa, Factor X, Factor Xa, Factor XI, Factor XIa, Factor XII, Factor XIIa, Factor XIII, Factor XIIIa, fibronectin, fibrinogen (Factor I), heparin cofactor II, high-molecular-weight kininogen (HMWK), intramuscular immunoglobulin, intravenous immunoglobulin, plasmin, plasminogen, plasminogen activator inhibitor-1 (PAI1), plasminogen activator inhibitor-2 (PAI2), prekallikrein, prostacyclin, protein C, active protein C (APC), protein S, protein Z, protein Z-related protease inhibitor, thrombomodulin, tissue factor (Factor III), Tissue factor pathway inhibitor (TFPI), tissue plasminogen activator (t-PA), urokinase, or Von Willebrand Factor.
30. The method of embodiment 26, wherein the pharmaceutical active ingredient is a biologic or a biosimilar.
31. The method of embodiment 26, wherein the pharmaceutical active ingredient is an antibody, an enzyme, or a toxin.
32. The method of embodiment 31, wherein the antibody is Abciximab, Adalimumab, Alemtuzumab, Basiliximab, Belimumab, Bevacizumab, Brentuximab Vedotin, Canakinumab, Certolizumab pegol, Cetuximab, Daclizumab, Denosumab, Efalizumab, Eculizumab, Gemtuzumab ozogamicin, Golimumab, Ibritumomab tiuxetan, Infliximab, Ipilimumab, Motavizumab, Muronomab, Natalizumab, Ofatumumab, Omalizumab, Palivizumab, Panitumumab, Ranibizumab, Raxibacumab, Rituximab, Tocilizumab, Tositumomab, Trastuzumab, or Ustekinumab.
33. The method of embodiment 26, wherein the pharmaceutical active ingredient is a polypeptide or peptidomemetic designed to have a beneficial effect when given to an individual.
34. The method of embodiment 26, wherein the excipient is albumin.
35. The method of embodiments 1-34, wherein data from an electrical sensing parameter is not collected by the particle analyzer.
36. The method of embodiments 1-35, wherein the electrical sensing parameter is DC impedance, RF conductivity, opacity, or a combination thereof.
37. The method of embodiments 1-36, wherein the particle analyzer is a flow cytometer.
38. The method of embodiments 1-37, wherein the particle size based upon the size standard calibration comprising sizes less than or equal to 10 μm, less than or equal to 20 μm, less than or equal to 50 μm, less than or equal to 75 μm, less than or equal to 100 μm, less than or equal to 200 μm, or less than or equal to 300 μm.
39. A method of characterizing a population of subvisible particles in a sample, the method comprising the steps of: a) calibrating a particle analyzer using a size standard; b) interrogating the sample as the sample passes through a sensing zone of the particle analyzer, the sample comprising a fluorescent counting standard and at least one fluorescent dye, wherein the interrogation includes one or more wavelengths that can interrogate the size standard, interrogate or excite the fluorescent counting standard, and interrogate or excite the at least one fluorescent dye, and wherein the at least one fluorescent dye includes a first fluorescent dye that stains a non-proteinaceous material in a manner that distinguishes the non-proteinaceous material from a proteinaceous material, and a second fluorescent dye that stains a physical property of the non-proteinaceous material in a manner that distinguishes a non-proteinaceous material having the physical property from a non-proteinaceous material not having the physical property; c) collecting data from at least one light scatter parameter and at least one fluorescence parameter, wherein the data collected from the at least one light scatter parameter represents a particle size based upon the size standard calibration, and wherein the data collected from the at least one fluorescence parameter includes a first fluorescence parameter representing presence of the non-proteinaceous material based upon fluorescence intensity emitted from the first fluorescent dye, a second fluorescence parameter representing a particle number based upon fluorescence intensity emitted from the fluorescent counting standard, and a third fluorescence parameter representing presence of the non-proteinaceous material having the physical property based upon fluorescence intensity emitted from the second fluorescent dye; and d) analyzing the data to define the particle size, the particle number, presence of the non-proteinaceous material, and presence of the physical property in order to determine absolute number and size of the non-proteinaceous subvisible particles with and without the physical property, thereby characterizing the population of subvisible particles in the sample.
40. A method of characterizing a population of subvisible particles in a sample, the method comprising the steps of: a) calibrating a particle analyzer using a size standard; b) interrogating the sample as the sample passes through a sensing zone of the particle analyzer, the sample comprising a fluorescent counting standard and at least one fluorescent dye, wherein the interrogation includes one or more wavelengths that can interrogate the size standard, interrogate or excite the fluorescent counting standard, and interrogate or excite the at least one fluorescent dye, and wherein the at least one fluorescent dye includes a first fluorescent dye that stains a non-proteinaceous material in a manner that distinguishes the non-proteinaceous material from a proteinaceous material; c) collecting data from at least one light scatter parameter and at least one fluorescence parameter, wherein the data collected from the at least one light scatter parameter represents a particle size based upon the size standard calibration, and wherein the data collected from the at least one fluorescence parameter includes a first fluorescence parameter representing presence of the non-proteinaceous material based upon fluorescence intensity emitted from the first fluorescent dye, and a second fluorescence parameter representing a particle number based upon fluorescence intensity emitted from the fluorescent counting standard; and d) analyzing the data to define the particle size, the particle number, and presence of the non-proteinaceous material in order to determine an absolute number and size of non-proteinaceous subvisible particles, thereby characterizing the population of subvisible particles in the sample.

41. The method of embodiment 40, wherein the data analysis step further comprises determining an absolute number of a sized proteinaceous subvisible particles by subtracting an absolute number of all sized subvisible particles by the absolute number of the sized non-proteinaceous subvisible particles.

42. The method of embodiment 40 or 41, wherein in the interrogating the sample step: the at least one fluorescent dye includes a second fluorescent dye that stains a physical property of the non-proteinaceous material in a manner that distinguishes a non-proteinaceous material having the physical property from a non-proteinaceous material not having the physical property, and the interrogation includes one or more wavelengths that can excite the second fluorescent dye; in the collection data step: collecting data further includes collecting data from a third fluorescence parameter, the third fluorescence parameter representing presence of the non-proteinaceous material having the physical property based upon fluorescence intensity emitted from the second fluorescent dye; and in the data analysis step: analyzing the data to define presence of the physical property in order to determine the fraction of counted, sized non-proteinaceous subvisible particles with or without the physical property, thereby characterizing the population of subvisible particles in the sample.

43. A method of characterizing a population of subvisible particles in a sample, the method comprising the steps of: a) calibrating a particle analyzer using a size standard; b) interrogating the sample as the sample passes through a sensing zone of the particle analyzer, the sample comprising at least one fluorescent dye, wherein the interrogation includes one or more wavelengths that can interrogate the size standard, and excite the at least one fluorescent dye, and wherein the at least one fluorescent dye includes a first fluorescent dye that stains a non-proteinaceous material in a manner that distinguishes the non-proteinaceous material from a proteinaceous material; c) collecting data from at least one light scatter parameter and at least one fluorescence parameter, wherein the data collected from the at least one light scatter parameter represents a particle size based upon the size standard calibration, and wherein the data collected from the at least one fluorescence parameter includes a first fluorescence parameter representing presence of the non-proteinaceous material based upon fluorescence intensity emitted from the first fluorescent dye; and d) analyzing the data to define the particle size and presence of the non-proteinaceous material in order to determine a size and presence of non-proteinaceous subvisible particles, thereby characterizing the population of subvisible particles in the sample.

44. The method of embodiments 39-43, wherein the size standard comprises particles having mean diameters of 0.5 µm, 1.0 µm, 2.0 µm, 4.5 µm, 6.0 µm, 10 µm, or a combination thereof.

45. The method of embodiments 39-44, wherein the first fluorescent dye has a peak fluorescence excitation wavelength from between about 300 nm to about 635 nm.

46. The method of embodiments 39-45, wherein the first fluorescent dye has a peak fluorescence emission wavelength from between about 350 nm to about 800 nm.

47. The method of embodiments 39-46, wherein the first fluorescent dye has a peak fluorescence excitation wavelength of about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, or about 630 nm.

48. The method of embodiments 39-47, wherein the first fluorescent dye has a peak fluorescence emission wavelength of about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, about 630 nm, about 640 nm, about 650 nm, about 660 nm, about 670 nm, about 680 nm, about 690 nm, about 700 nm, about 710 nm, about 720 nm, about 730 nm, about 740 nm, about 750 nm, about 760 nm, about 770 nm, about 780 nm, about 790 nm, or about 800 nm.

49. The method of embodiments 39-48, wherein the first fluorescent dye is a lipophilic dye.

50. The method of embodiment 49, wherein the lipophilic dye is a carbocyanine lipophilic dye, a lipophilic aminostyryl dye, an amphiphilic styryl dye, a dialkylaminostyryl dye, an amphiphilic probe, a nonpolar probe, a membrane probe, or a lipophilic cation probe.

51. The method of embodiments 43-50, wherein in the interrogating the sample step: the sample further comprises a fluorescent counting standard, and the interrogation includes one or more wavelengths that can interrogate or excite the fluorescent counting standard; and in the collection data step: the at least one fluorescence parameter includes a second fluorescence parameter representing a particle number based upon fluorescence intensity emitted from the fluorescent counting standard; in the data analysis step: analyzing the data to define the particle number in order to determine an absolute number of the sized non-proteinaceous subvisible particles, thereby characterizing the population of subvisible particles in the sample.

52. The method of embodiments 39-42 or 49-51, wherein the fluorescent counting standard comprises particles having a peak fluorescence excitation wavelength from between about 300 nm to about 635 nm.

53. The method of embodiments 39-42 or 49-52, wherein the fluorescent counting standard comprises particles having a peak fluorescence emission wavelength from between about 385 nm and about 800 nm.

54. The method of embodiments 49-53, wherein the data analysis step further comprises determining an absolute number of sized proteinaceous subvisible particles by subtracting an absolute number of all sized subvisible particles by the absolute number of sized non-proteinaceous subvisible particles.

55. The method of embodiments 49-54, wherein in the interrogating the sample step: the at least one fluorescent dye includes a second fluorescent dye that stains a physical property of the non-proteinaceous material in a manner that distinguishes a non-proteinaceous material having the physical property from a non-proteinaceous material not having the physical property, and the interrogation includes one or more wavelengths that can excite the second fluorescent dye; and in the collection data step: collecting data further includes collecting data from a third fluorescence parameter, the third fluorescence parameter representing presence of the non-proteinaceous material having the physical property based upon fluorescence intensity emitted from the second fluorescent dye; in the data analysis step: analyzing the data to define presence of the physical property in order to determine a fraction of counted, sized non-proteinaceous subvisible particles with or without the physical property, thereby characterizing the population of subvisible particles in the sample.

56. The method of embodiments 39, 42, or 55, wherein the physical property is a structural feature or chemical modification.

57. The method of embodiments 39, 42, 55, or 56, wherein the second fluorescent dye has a peak fluorescence excitation wavelength from between about 350 nm to about 635 nm.

58. The method of embodiments 39, 42, or 53-55, wherein the second fluorescent dye has a peak fluorescence emission wavelength from between about 350 nm to about 800 nm.

59. The method of embodiments 39, 42, or 55-58, wherein the second fluorescent dye has a peak fluorescence excitation wavelength of about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, or about 630 nm.

60. The method of embodiments 39, 42, or 55-59, wherein the second fluorescent dye has a peak fluorescence emission wavelength of about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, about 630 nm, about 640 nm, about 650 nm, about 660 nm, about 670 nm, about 680 nm, about 690 nm, about 700 nm, about 710 nm, about 720 nm, about 730 nm, about 740 nm, about 750 nm, about 760 nm, about 770 nm, about 780 nm, about 790 nm, or about 800 nm.

61. The method of embodiments 39-60, wherein the sample is a pharmaceutical preparation.

62. The method of embodiment 61, wherein the pharmaceutical preparation comprises a proteinaceous material that is a pharmaceutical active ingredient, an adjuvant, or an excipient.

63. The method of embodiment 62, wherein the pharmaceutical active ingredient is a blood protein.

64. The method of embodiment 62, wherein the pharmaceutical active ingredient is a blood coagulation protein.

65. The method of embodiment 62, wherein the pharmaceutical active ingredient is ADAMTS-13, α1-antiplasmin, α2-antiplasmin, antithrombin, antithrombin III, cancer procoagulant, erythropoietin, Factor II, Factor IIa, Factor V, Factor Va, Factor VI, Factor VIa, Factor VII, Factor VIIa, Factor VIII, Factor VIIIa, Factor IX, Factor IXa, Factor X, Factor Xa, Factor XI, Factor XIa, Factor XII, Factor XIIa, Factor XIII, Factor XIIIa, fibronectin, fibrinogen (Factor I), heparin cofactor II, high-molecular-weight kininogen (HMWK), intramuscular immunoglobulin, intravenous immunoglobulin, plasmin, plasminogen, plasminogen activator inhibitor-1 (PAI1), plasminogen activator inhibitor-2 (PAI2), prekallikrein, prostacyclin, protein C, active protein C (APC), protein S, protein Z, protein Z-related protease inhibitor, thrombomodulin, tissue factor (Factor III), Tissue factor pathway inhibitor (TFPI), tissue plasminogen activator (t-PA), urokinase, or Von Willebrand Factor.

66. The method of embodiment 62, wherein the pharmaceutical active ingredient is a biologic or a biosimilar.

67. The method of embodiment 62, wherein the pharmaceutical active ingredient is an antibody, an enzyme, or a toxin.

68. The method of embodiment 67, wherein the antibody is Abciximab, Adalimumab, Alemtuzumab, Basiliximab, Belimumab, Bevacizumab, Brentuximab Vedotin, Canakinumab, Certolizumab pegol, Cetuximab, Daclizumab, Denosumab, Efalizumab, Eculizumab, Gemtuzumab ozogamicin, Golimumab, Ibritumomab tiuxetan, Infliximab, Ipilimumab, Motavizumab, Muronomab, Natalizumab, Ofatumumab, Omalizumab, Palivizumab, Panitumumab, Ranibizumab, Raxibacumab, Rituximab, Tocilizumab, Tositumomab, Trastuzumab, or Ustekinumab.

69. The method of embodiment 62, wherein the pharmaceutical active ingredient is a polypeptide or peptidomemetic designed to have a beneficial effect when given to an individual.

70. The method of embodiment 62, wherein the excipient is albumin.

71. The method of embodiments 39-70, wherein data from an electrical sensing parameter is not collected by the particle analyzer.

72. The method of embodiments 39-71, wherein the electrical sensing parameter is DC impedance, RF conductivity, opacity, or a combination thereof.

73. The method of embodiments 39-72, wherein the particle analyzer is a flow cytometer.

74. The method of embodiments 39-73, wherein the particle size based upon the size standard calibration comprising sizes less than or equal to 10 μm, less than or equal to 20 μm, less than or equal to 50 μm, less than or equal to 75 μm, less than or equal to 100 μm, less than or equal to 200 μm, or less than or equal to 300 μm.

75. The method of embodiments 1-74 substantially as described herein.

76. A method of characterizing a population of subvisible particles in a sample substantially described herein.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of characterizing subvisible particles.

Example 1

Establishing Limits of Size Detection and Size Distribution Ranges

To be able to establish size distribution ranges a size standard stock solution was prepared from Fluoresbright Size Calibration Kit I and II (Polysciences, Inc., Warrington, PA). This stock solution included microspheres having mean diameters of 0.75 µm, 1.0 µm, 2.0 µm, 4.5 µm, 6.0 µm and 10 µm and was prepared according to the manufacturer's instructions.

The prepared test sample was analyzed using a BD LSRFORTESSA™ particle analyzer (Becton Dickinson, San Jose, CA) equipped with a 405-nm violet laser, a 488-nm blue laser, a 561-nm yellow/green laser and a 635-nm red laser; and having two 488-nm light scattering detectors (low-angle forward scattering [FSC] and 90° side scattering [SSC]) and 16 fluorescence detectors. The forward and the side scatter were illustrated logarithmically. A threshold was set on the forward and side scatter in a manner that would include particles on the forward scatter vs. side scatter plot but still exclude electronic noise. All events were analyzed and recorded for 120 seconds in the "high" sample flow instrument option, or about 60 µL/min. All analyses of flow cytometry data were performed using FACS Diva Software 6.0 (Becton Dickinson, San Jose, CA) or FlowJo 8.8.6 (Tree Star, Ashland, OR). To define different size ranges, gates were set between the peak maxima of each size calibration bead population in a FSC histogram. The settings and gates were stored as a template and reused on different analyzing days after rechecking with calibration beads.

Figure 1B:
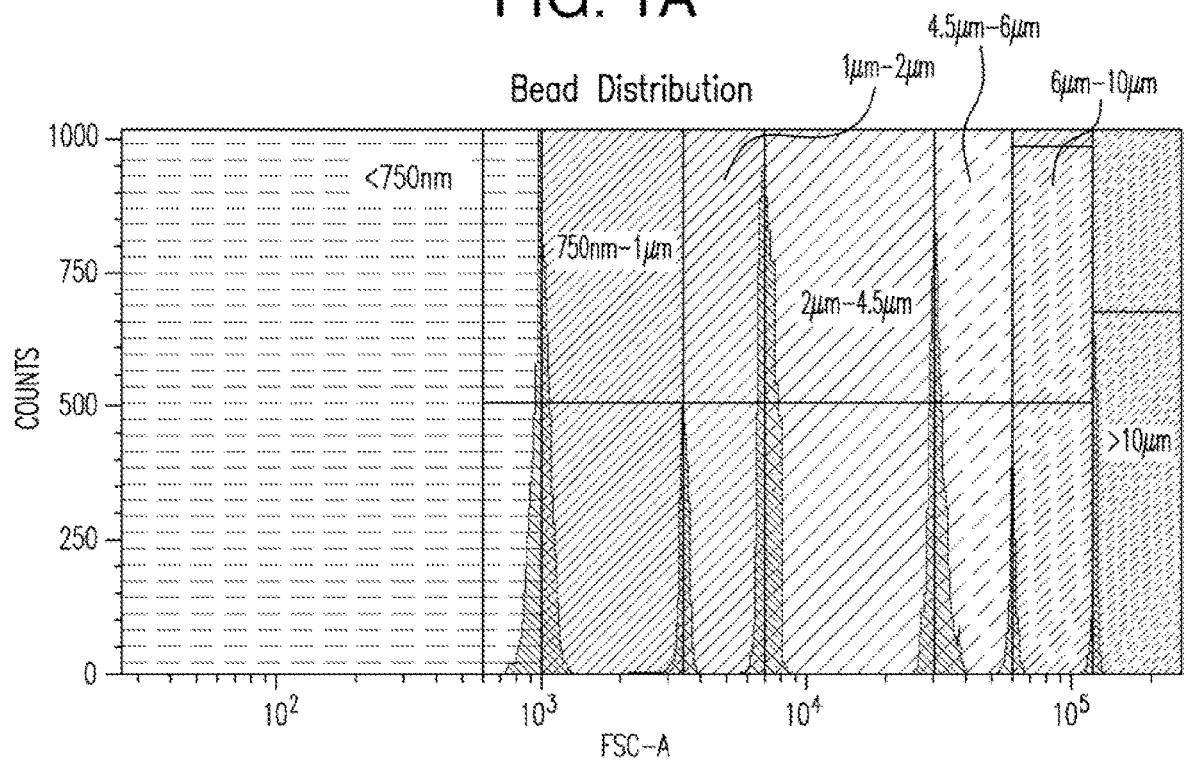

Analysis of the data indicated that particles of about 0.75 µm, about 1.0 µm, about 2.0 µm, about 4.5 µm, about 6.0 µm, and about 10 µm were detected (FIG. 1A). The results show that particles of less than 200 µm from a counting standard can be detected and sized. Analysis of the data also enabled the generation of particle size distribution ranges of less than about 0.75 µm, about 0.75 µm to about 1.0 µm, about 1.0 µm to about 2.0 µm, about 2.0 µm to about 4.5 µm, about 4.5 µm to about 6.0 µm, about 6.0 µm to about 10 µm, and about 10 µm to about 200 µm (FIG. 1B) and the placement of each detected particle into one of these size distribution ranges. These results showed that particles can be classified into a size distribution range comprising categories less than or equal to 200 µm.

Example 2

Establishing Limits of Size Detection and Size Distribution Ranges

To be able to establish size distribution ranges a size standard stock solution was prepared from Fluoresbright Size Calibration Kit I and II (Polysciences, Inc., Warrington, PA). This stock solution included microspheres having mean diameters of 0.75 µm, 1.0 µm, 2.0 µm, 4.5 µm, 6.0 µm and 10 µm and was prepared according to the manufacturer's instructions.

The prepared test sample was analyzed using a BD FACSARIAIII™ particle analyzer (Becton Dickinson, San Jose, CA) equipped with a 405-nm violet laser, a 488-nm blue laser and a 633-nm red laser; and having two 488-nm light scattering detectors (low-angle forward scattering [FSC] and 90° side scattering [SSC]) and 11 fluorescence detectors. The forward and the side scatter were illustrated logarithmically. A threshold was set on the forward and side scatter in a manner that would include particles on the forward scatter vs. side scatter plot but still exclude electronic noise. All events were analyzed and recorded for 300 seconds running always at the same low sample flowrate (using a Diva Software Flowrate of 2). All analyses of flow cytometry data were performed using FACS Diva Software 6.0 (Becton Dickinson, San Jose, CA) or FlowJo 8.8.6 (Tree Star, Ashland, OR). To define different size ranges, gates were set between the peak maxima of each size calibration bead population and the end of the axes in a FSC histogram. The settings and gates were stored as a template and reused on different analyzing days after rechecking with calibration beads.

Figure 2A:
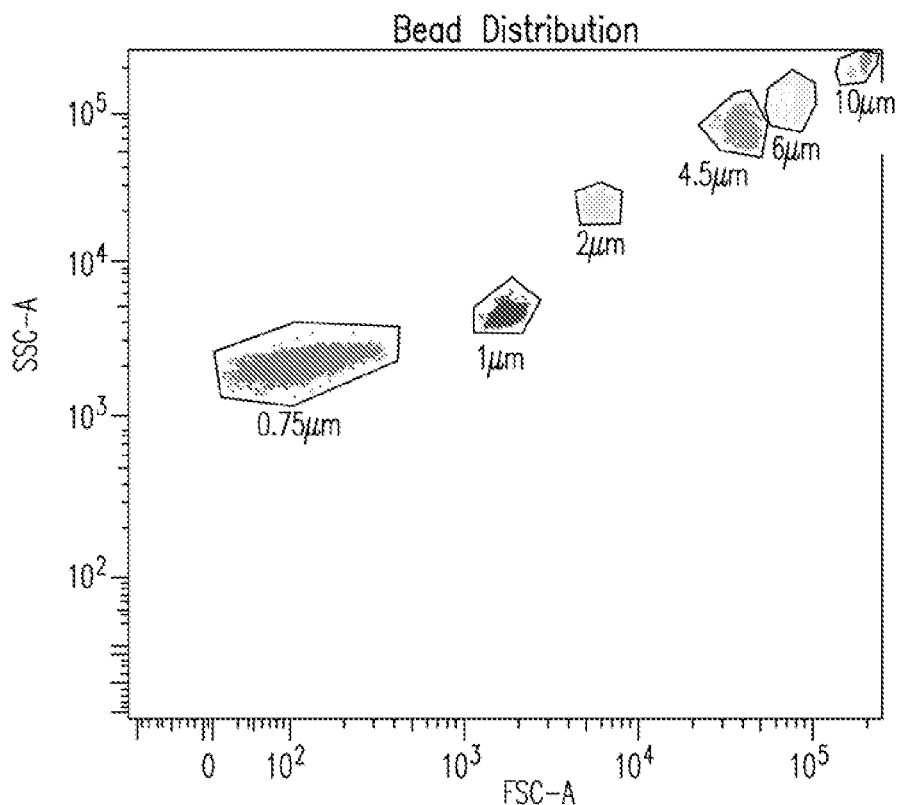
FIGS. 2A and 2B shows data representing particle size (A) and size distribution range (B) generated setting gates between the peak maxima of each size standard bead and the end of the axes. For FIG. 2B, the tracings represents particle sizes from about 0.75 µm to about less than 10 µm, from about 1.0 µm to less than about 10 µm, from about 2.0 µm to less than about 10 µm, from about 4.5 µm to less than about 10 µm, from about 6.0 µm to less than about 10 µm, and greater than about 10 µm.
Figure 2B:
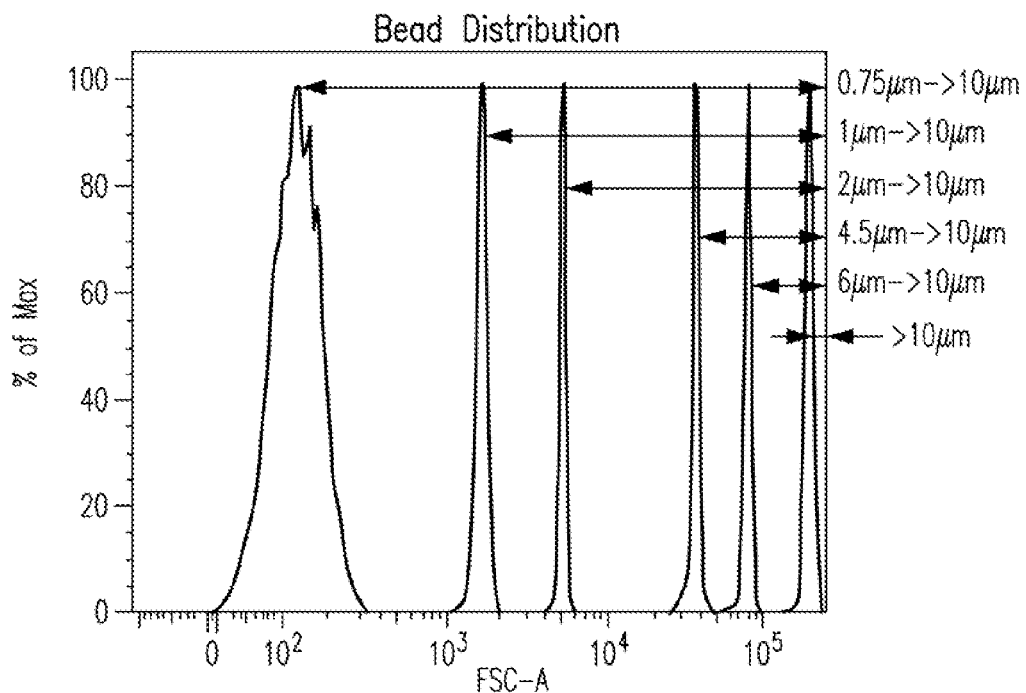

Analysis of the data indicated that particles of about 0.75 µm, about 1.0 µm, about 2.0 µm, about 4.5 µm, about 6.0 µm, and about 10 µm were detected (FIG. 2A). The results show that particles of less than the diameter of the sample tubing (i.e., less than 200 µm) used in the flow cytometer can be detected and sized. The results show that particles of less than 200 µm from a counting standard can be detected and sized. Analysis of the data also enabled the generation of particle size distribution ranges of less than about 0.75 µm, about 0.75 µm to about 1.0 µm, about 1.0 µm to about 2.0 µm, about 2.0 µm to about 4.5 µm, about 4.5 µm to about 6.0 µm, about 6.0 µm to about 10 µm, and from 10 µm to about the upper limit of detection, which is determined by the diameter of the sample tubing (around 200 µm) (FIG. 2B) and the placement of each detected particle into one of these size distribution ranges. These results showed that particles can be classified into a size distribution range comprising categories less than or equal to 200 µm.

Example 3

Detecting, Counting and Determination of Size Distribution of Particles

To prepare a test sample, 50 µL (about 49,500 microspheres) of COUNTBRIGHT™ Absolute Counting Beads (Invitrogen, Life Technologies Ltd., Paisley, Great Britain) were added to 450 µL of a particle sample including 50 µg/mL amyloid β peptide 1-42 aggregates.

The prepared test sample was analyzed using a BD LSRFORTESSA™ particle analyzer (Becton Dickinson, San Jose, CA) as described in Example 1. The stored settings, thresholds, and gates determined by the size standard in Example 1 were used as a template for size distribution ranges. All events were analyzed, recorded, and evaluated as described in Example 1. Each sample was evaluated three times and a mean value and standard deviations of the three results were calculated. A control sample comprising formulation buffers was analyzed in parallel to record the background signal for the corresponding test sample. Background signals were subtracted from the sample signal in the final analyses.

Figure 3A:
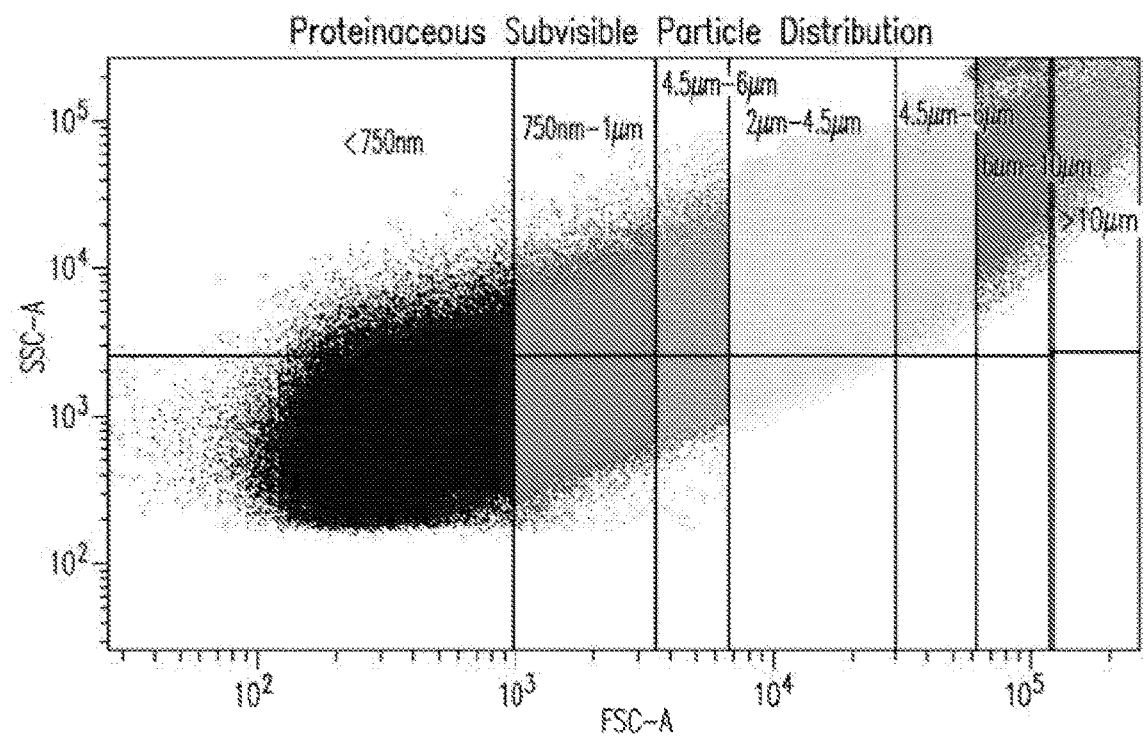
FIGS. 3A-3C shows data representing proteinaceous subvisible particle size distribution range (A) and particle count within each distribution range (B) generated from forward light scatter and side light scatter parameters.
Figure 3B:
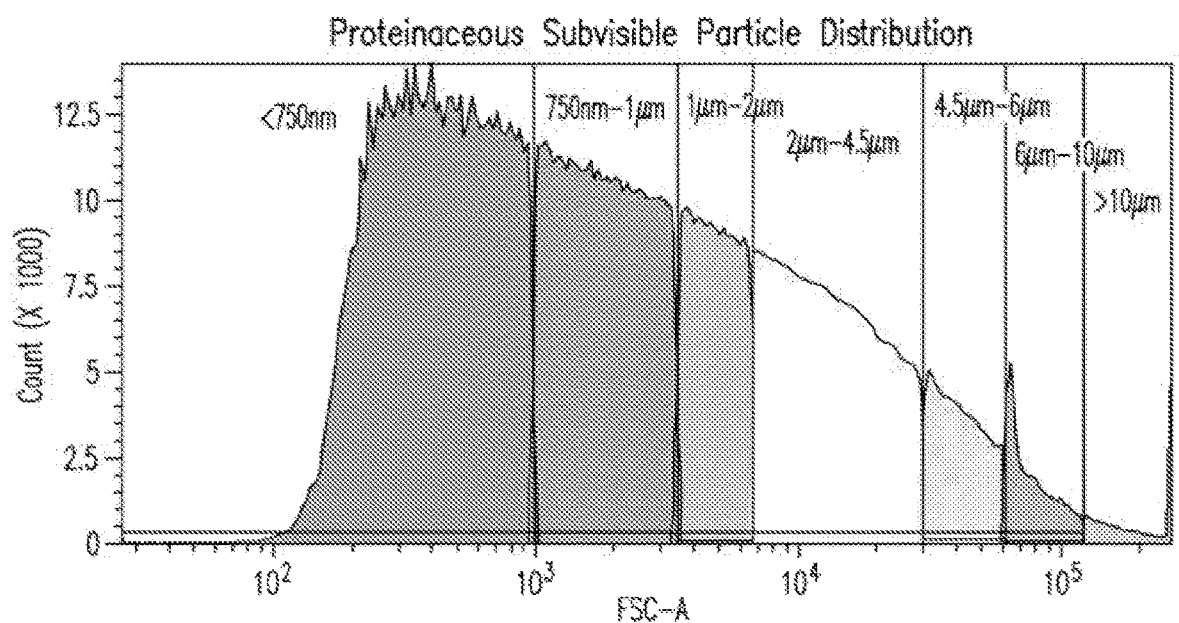
Figure 3C:
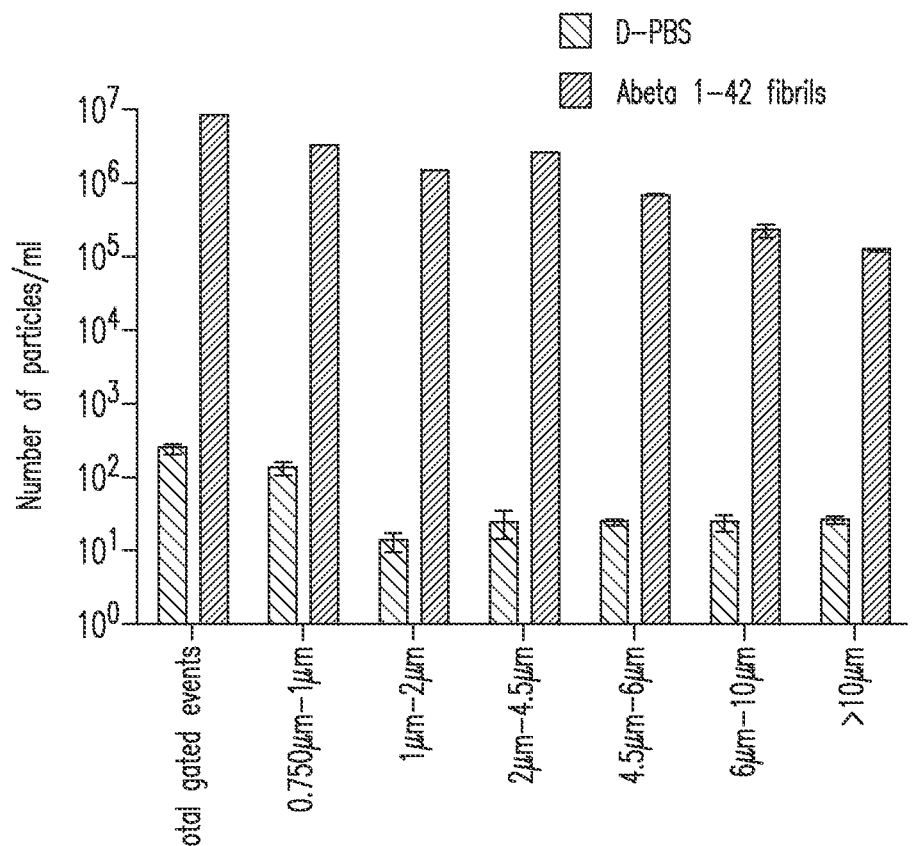

Analysis of the data determined the number of particles in the sample and placement of each particle into a specified size distribution range (FIGS. 3A, 3B, and 3C). These results show that proteinaceous particles can be detected, counted and classified into a size distribution range comprising categories less than or equal to 200 µm.

Example 4

Discrimination and Counting of Proteinaceous and Non-Proteinaceous Particles

In this experiment three test samples of 450 µL were prepared. The first test sample included 25 µg/mL amyloid β peptide 1-42 aggregates (proteinaceous particles), the second test sample included polydisperse latex microspheres (non-proteinaceous particles) and the third test sample included a mixture of both amyloid β peptide 1-42 aggregates and polydisperse latex microspheres (Polybead PMMA clear 1-10 µm microparticles; Polysciences, Inc., Warrington, PA). To all three samples 50 µL (about 49,500 microspheres) of COUNTBRIGHT™ Absolute Counting Beads (Invitrogen, Life Technologies Ltd., Paisley, Great Britain) were added according to the manufacturer's instructions. To this mixture, 1× SYPRO™ Orange (SO) (Invitrogen, Life Technologies Ltd., Paisley, Great Britain) was added.

The prepared test samples were analyzed using a BD LSRFORTESSA™ particle analyzer (Becton Dickinson, San Jose, CA) as described in Example 1. The stored settings, thresholds, and gates determined by the size standard in Example 1 were used as a template for size distribution ranges. Fluorescent intensity of 1× SYPRO™ Orange (SO) stained particles was detected using a blue laser with 530/30 bandpass filter. All events were analyzed, recorded, and evaluated as described in Example 3. A control sample comprising formulation buffers was analyzed in parallel to record the background signal for the corresponding test sample. Background signals were subtracted from the sample signal in the final analyses.

Figure 4A:
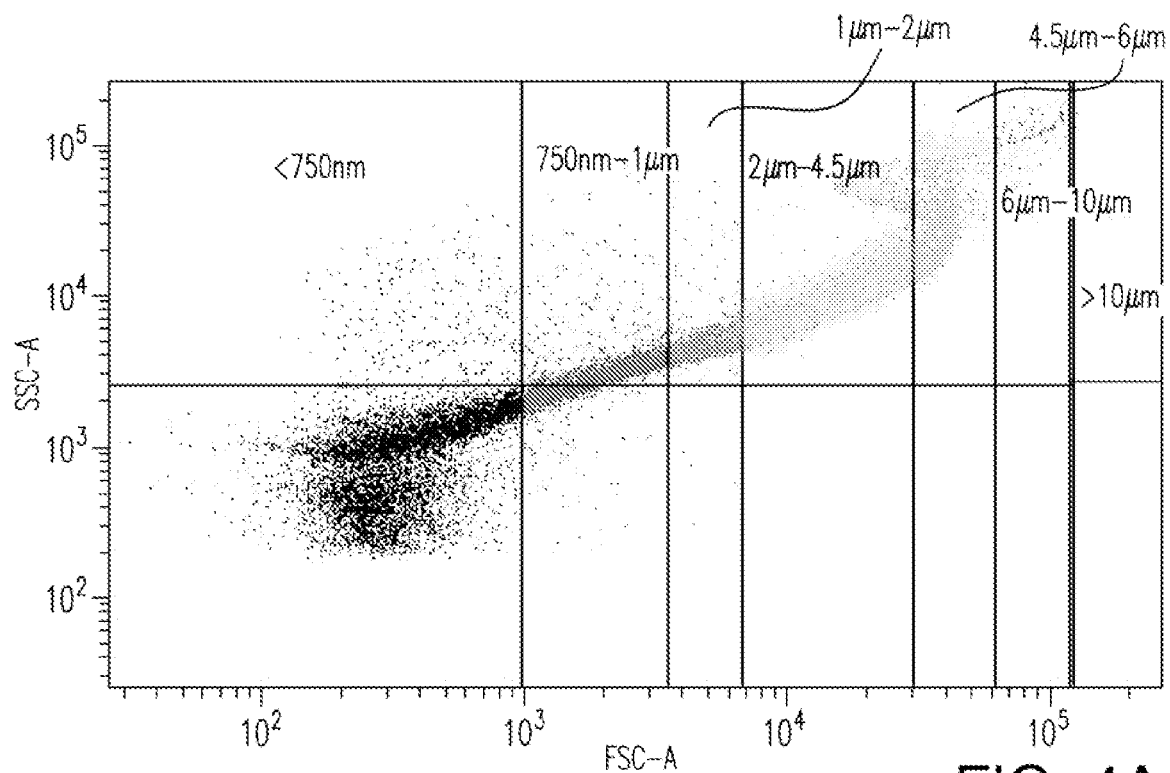
FIGS. 4A-4E shows data representing non-proteinaceous subvisible particle size distribution range (A) and proteinaceous subvisible particle size distribution range (B) generated from forward light scatter and side light scatter parameters.
Figure 4B:
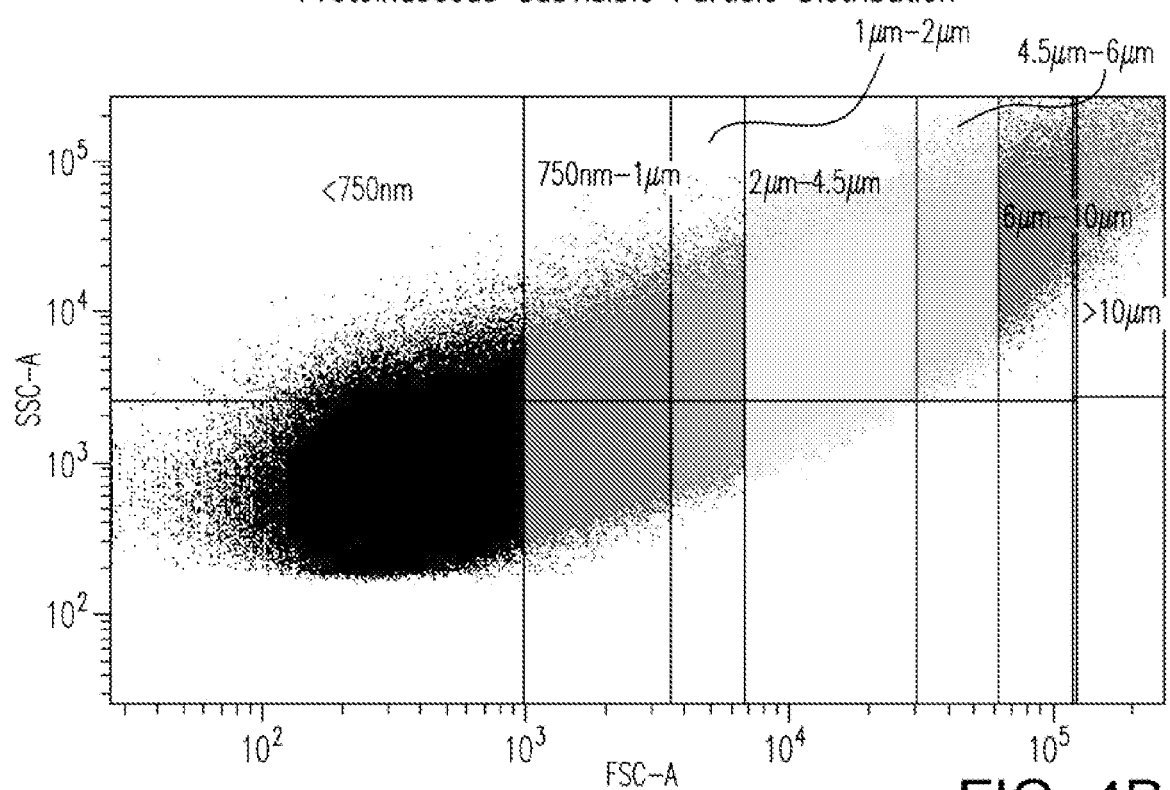
Figure 4C:
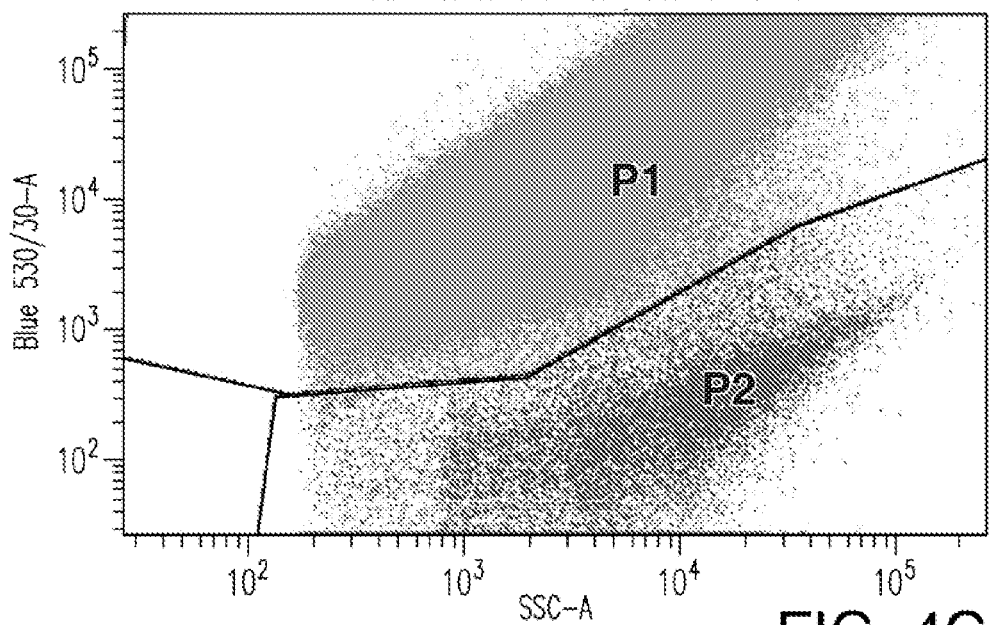
Figure 4D:
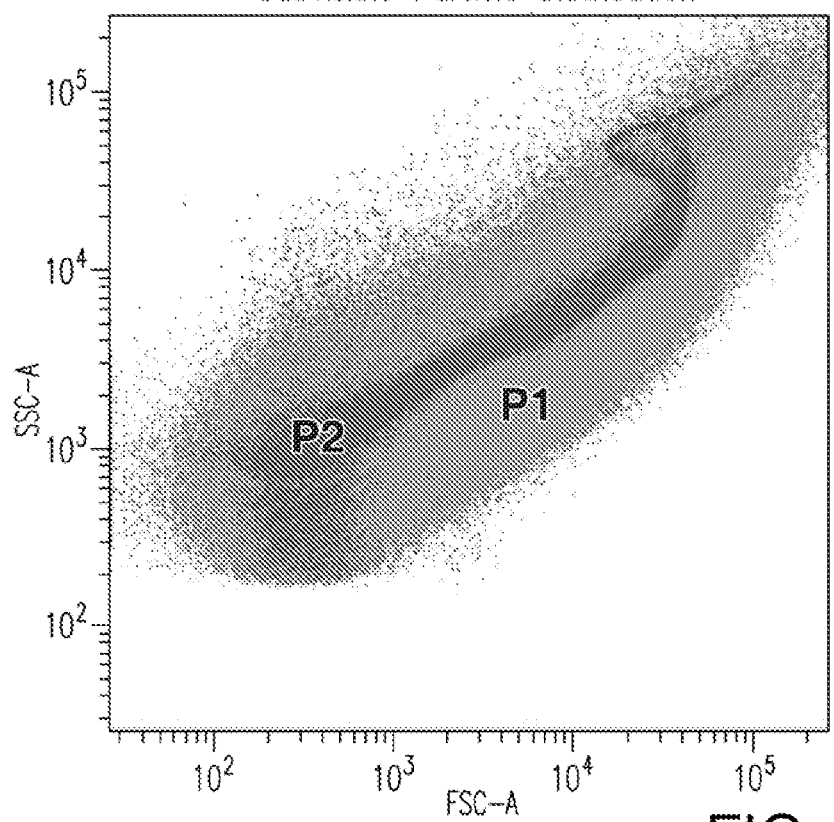
Figure 4E:
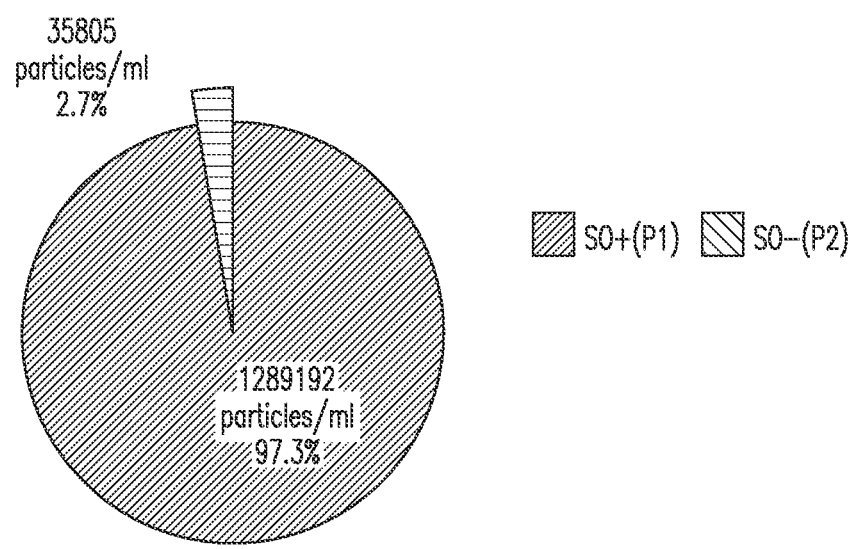

Analysis of the data determined both the number of non-proteinaceous particles in the sample and placement of each particle into a specified size distribution range (FIG. 4A) as well as the number of proteinaceous particles in the sample and placement of each particle into a specified size distribution range (FIG. 4B). These results show that both non-proteinaceous and proteinaceous particles can be detected, counted and classified into a size distribution range comprising categories less than or equal to 200 µm. Analysis of the data also detected and discriminated proteinaceous particles relative to non-proteinaceous particles based on SYPRO™ Orange staining (FIG. 4C) and allowed for the comparison of proteinaceous particles versus non-proteinaceous particles (FIG. 4D). These results also allowed the determination of the absolute numbers of proteinaceous and non-proteinaceous particles in the sample (FIG. 4E). These results show that both qualitative and quantitative assessment of proteinaceous and non-proteinaceous particles in a sample can be determined.

Example 5

Proteinaceous Subvisible Particle Characterization

A test sample of proteinaceous and non-proteinaceous particles was prepared as described in Example 3, except that Thioflavin T (ThT) was added to a concentration of 4 µM to these samples.

The prepared test sample was analyzed using a BD LSRFORTESSA™ particle analyzer (Becton Dickinson, San Jose, CA) as described in Example 1. The stored settings, thresholds, and gates determined by the size standard in Example 1 were used as a template for size distribution ranges. Fluorescent intensity was detected using a violet laser with a 525/50 bandpass filter and a blue laser with 530/30 bandpass filter. All events were analyzed, recorded, and evaluated as described in Example 2. A control sample comprising formulation buffers was analyzed in parallel to record the background signal for the corresponding test sample. Background signals were subtracted from the sample signal in the final analyses.

Figure 5A:
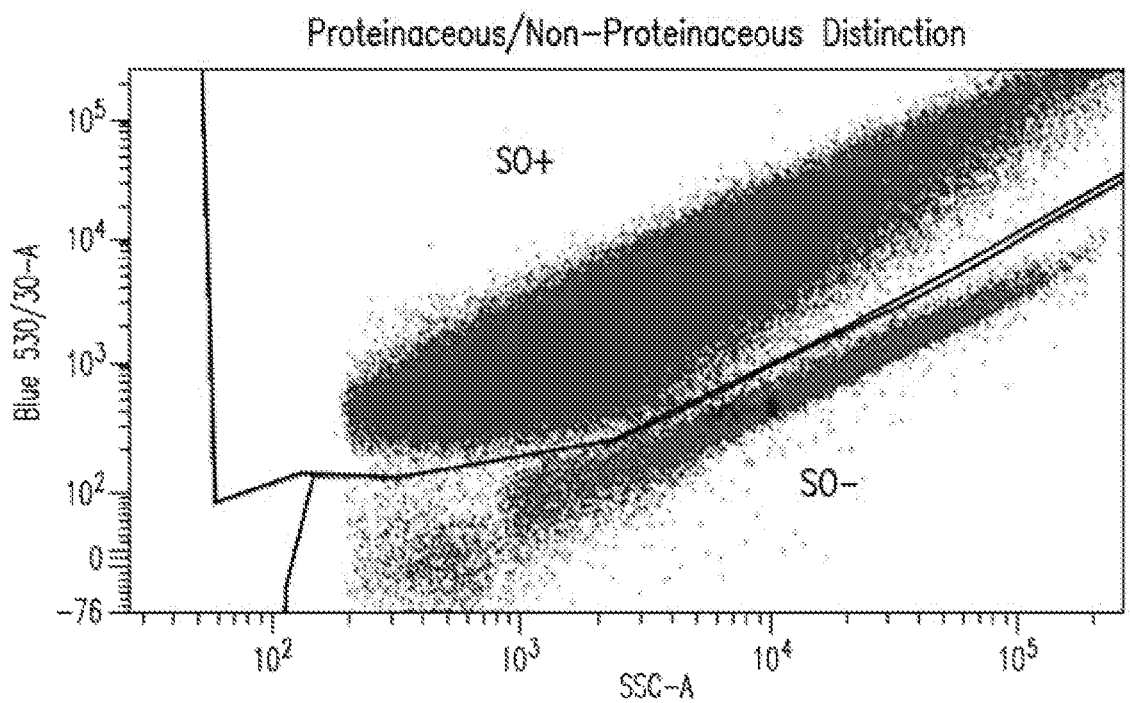
FIGS. 5A-5D shows data indicating that proteinaceous subvisible particles (SO+) and non-proteinaceous subvisible particles (SO−) can be discriminated from one another based on fluorescent intensity due to SYPRO™ Orange (SO) staining (A).
Figure 5B:
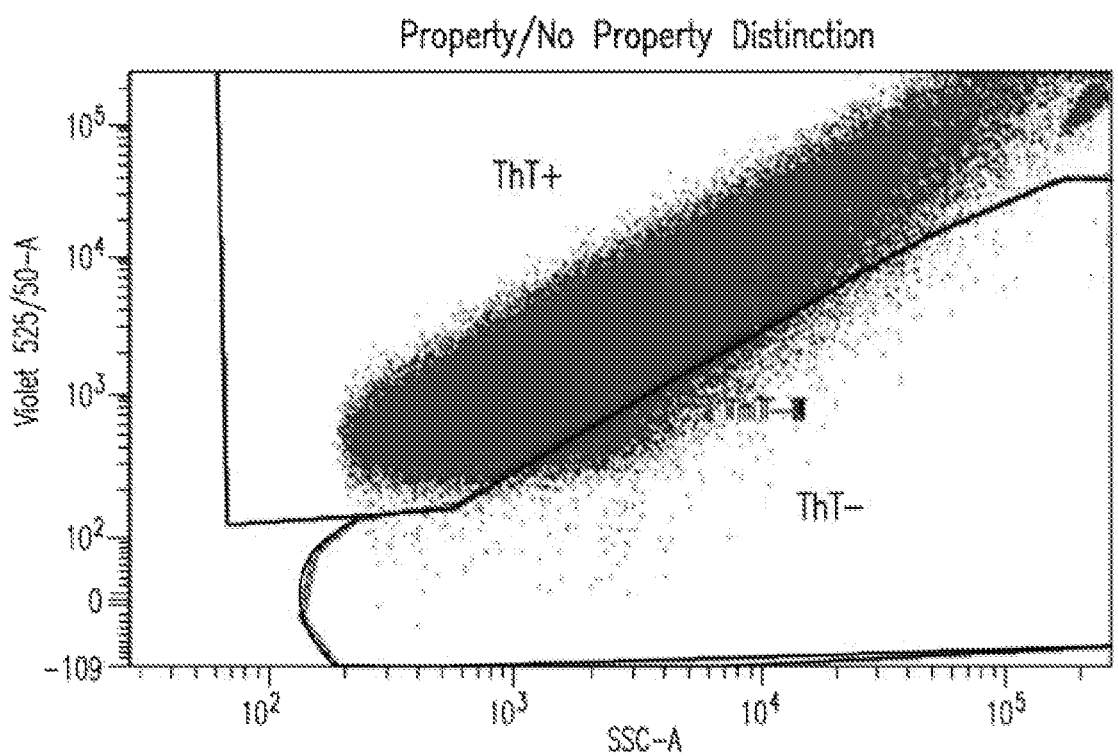
Figure 5C:
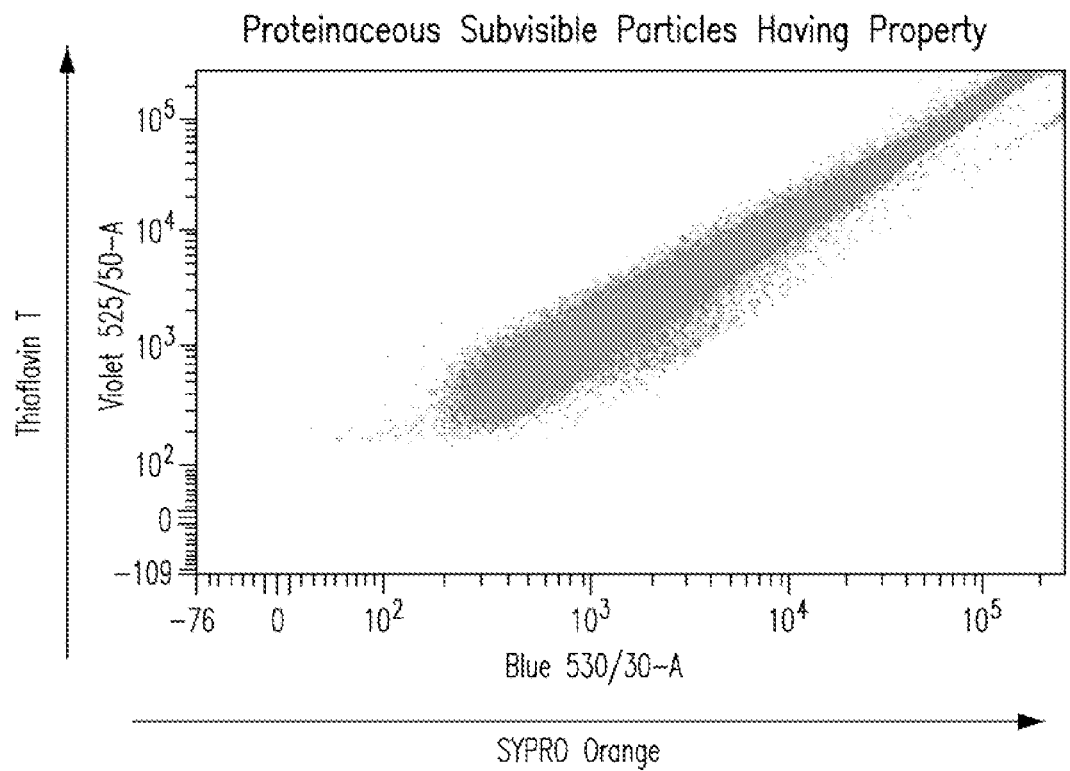
Figure 5D:
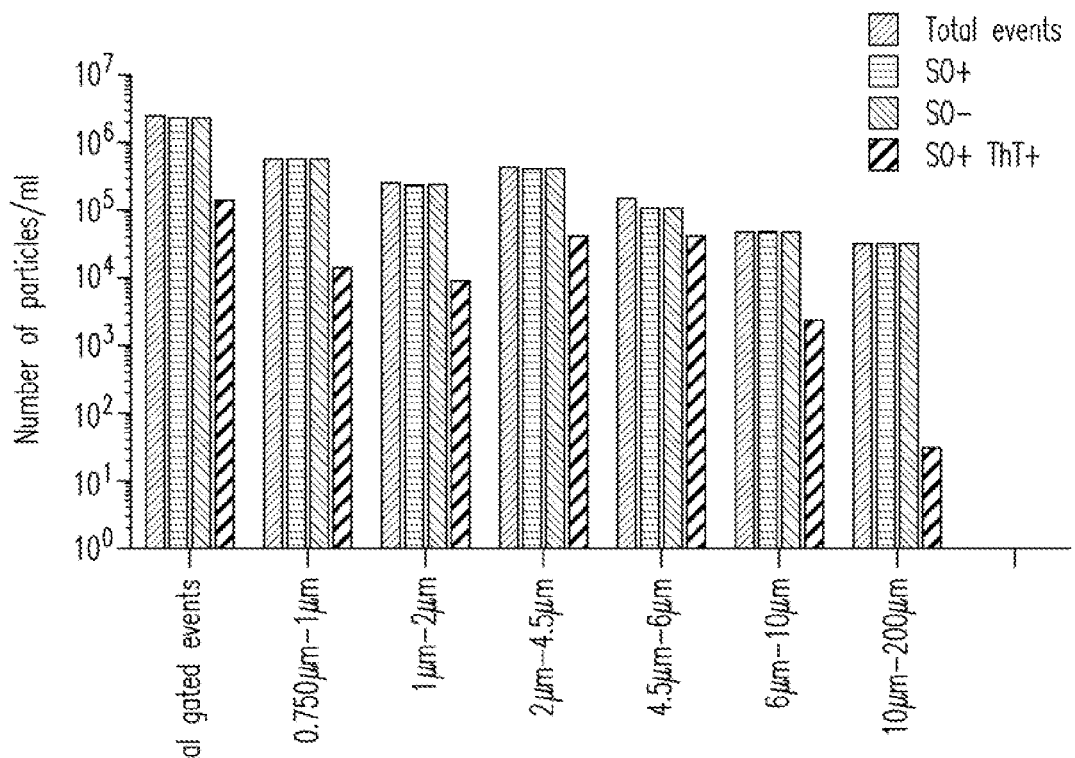

Analysis of the data detected and discriminated proteinaceous particles from non-proteinaceous particles based on SYPRO™ Orange staining (FIG. 5A) and detected and discriminated proteinaceous particles having a β-sheet structure from proteinaceous particles lacking this structure (FIG. 5B). These results also allowed the identification of proteinaceous particles having a β-sheet structure in the sample (FIG. 5C). These results also allowed the determination of the absolute numbers of non-proteinaceous particles, proteinaceous lacking a β-sheet structure, and proteinaceous particles having a β-sheet structure (FIG. 5D). These results show that both qualitative and quantitative assessment of non-proteinaceous particles and proteinaceous with and without a certain physical property in a sample can be determined.

Example 6

Detecting and Characterizing Subvisible Particles by Using a Multicolor Flow Panel In this experiment two test samples of 200 µL were prepared. The first test sample included 195 µL of a mixture of non-protein particles; the second test sample included 30 µL of 0.1 mg/mL glass beads of 3-10 µm as non-protein particles (Glass Beads 3-10 microns, Polysciences, Inc., Warrington, PA) and 165 µL of a mixture of Aβ peptide 1-42 subvisible particles and a protein subvisible particles containing low amounts of cross-β structures. To all samples Bis-ANS (Sigma-Aldrich, St. Louis, MO) to 20 µM final concentration and DCVJ (Sigma-Aldrich, St. Louis, MO) to 5 µM final concentration were added.

The prepared test samples were analyzed using a BD FACSARIAIII™ particle analyzer (Becton Dickinson, San Jose, CA) as described in Example 2. The stored settings, thresholds, and gates determined by the size standard in Example 2 were used as a template for size distribution ranges. All events were analyzed, recorded, and evaluated as described in Example 2. Each sample was evaluated three times and a mean value and standard deviations of the three results were calculated. A control sample comprising formulation buffers was analyzed in parallel to record the background signal for the corresponding test sample. Background signals were subtracted from the sample signal in the final analyses.

Figure 6A:
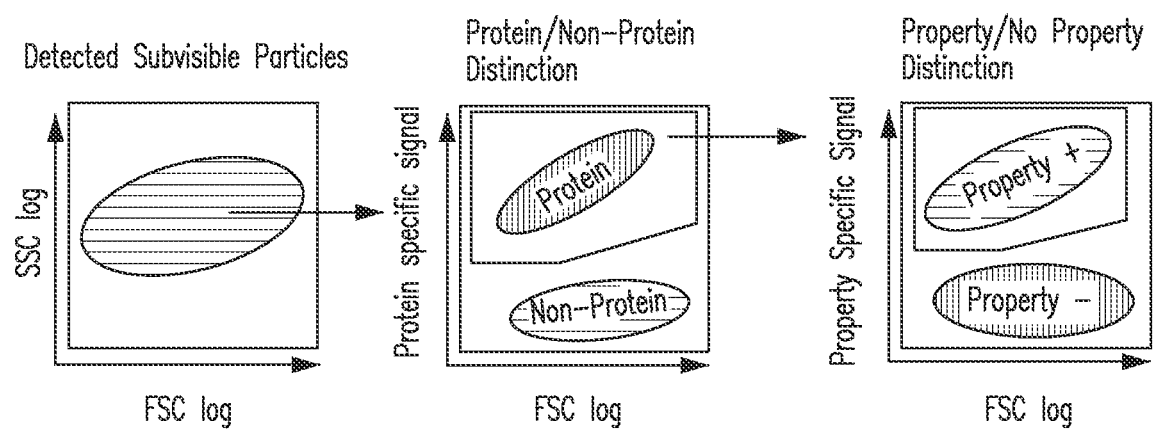
FIGS. 6A-6E shows the gating strategy used to discriminate at the same time in one sample between proteinaceous subvisible particles (Protein) and non-proteinaceous (Non-protein) as well as between the presence (Property +) or absence (Property −) of a property of proteinaceous subvisible particles (A).
Figures 6B, 6C, 6D:
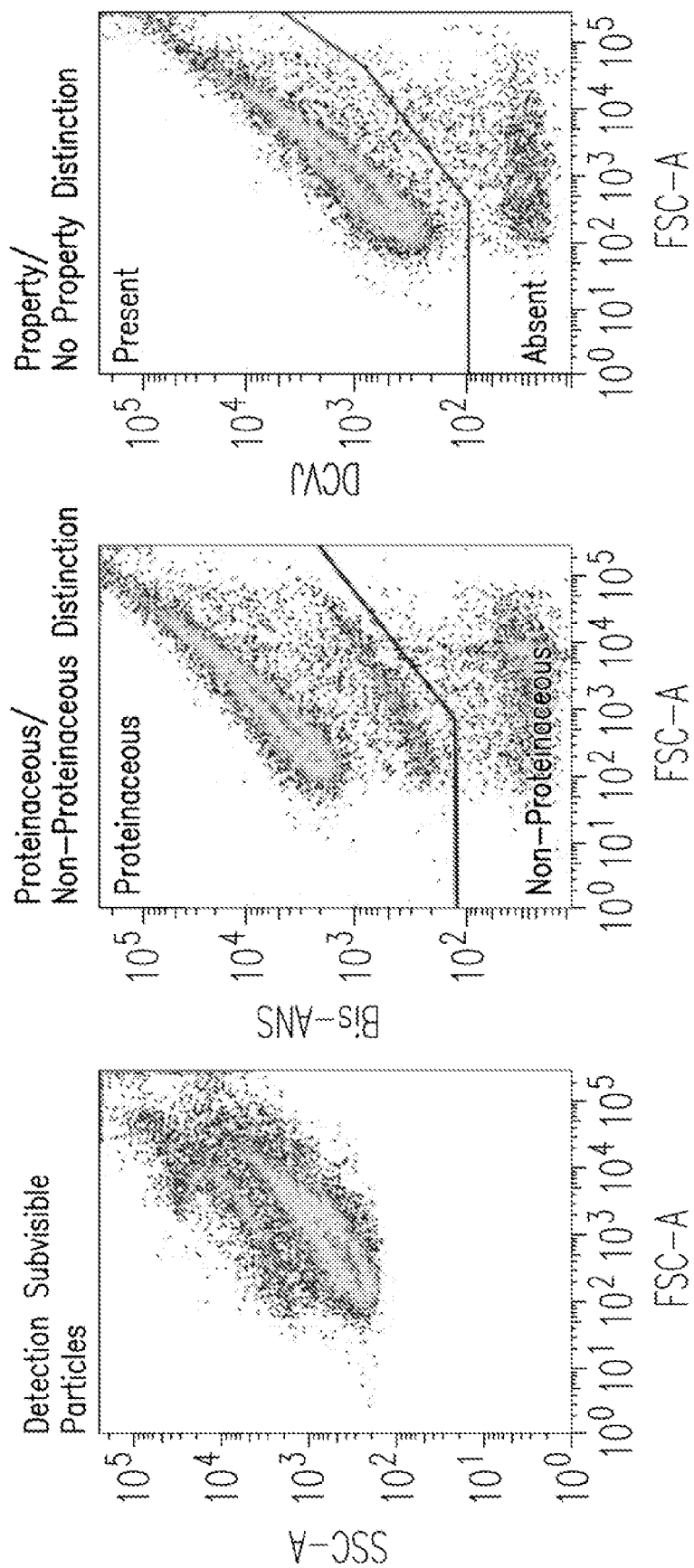
Figure 6E:
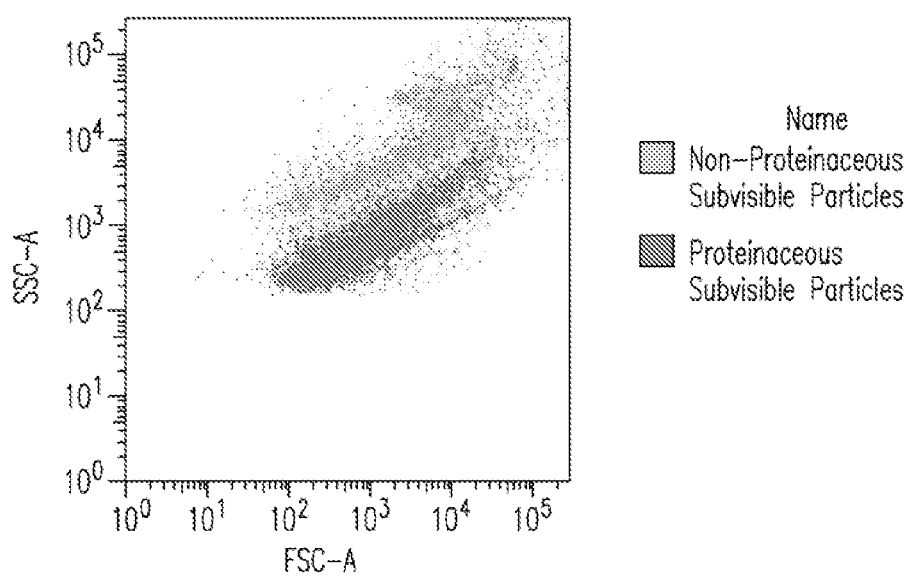

Analysis of sample 1 containing only non-protein particles enabled the setting of gates to determine non-protein containing particles. This gate was stored and used for the analysis of sample 2 containing a mixture of non-protein particles, protein containing particles and amyloid like particles. Analysis of the data from sample 2 detected and discriminated proteinaceous particles from non-proteinaceous particles based on Bis-ANS staining and detected and discriminated proteinaceous particles having a β-sheet structure from proteinaceous particles lacking this structure using DCVJ. This gating strategy is shown in Appendix FIG. 6A. The results obtained from sample 2 show that proteinaceous subvisible particles can be detected and discriminated from proteinaceous and non-protein particles using Bis-ANS, and can be further characterized for containing cross-β structures using DCVJ (FIG. 6B-6E). The sample data was first plotted in Forward Scatter against Side Scatter to detect subvisible particles within the sample (Appendix FIG. 6B). Bis-ANS was then used as the protein specific dye to discriminate between protein and non-protein containing particles (Appendix FIG. 6C). Protein containing particles were further characterized using DCVJ which binds specific to cross-β structures and enables the identification of amyloid like protein particles (Appendix FIG. 6D). Backgating analysis of protein and non-protein containing particles was also performed as shown in FIG. 6E.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of characterizing a population of subvisible particles in a sample, the method comprising the steps of:
   a) calibrating a particle analyzer using a size standard;
   b) adding a fluorescent counting standard and at least two dyes to the sample, wherein the at least two dyes comprise a first dye that stains a non-proteinaceous material in a manner that distinguishes the non-proteinaceous material from a proteinaceous material, and a second dye that stains a physical property of the non-proteinaceous material in a manner that distinguishes a non-proteinaceous material having the physical property from a non-proteinaceous material not having the physical property;
   c) interrogating the sample as the sample of step b) as the sample passes through a sensing zone of the particle analyzer, wherein the interrogation includes one or more wavelengths that can interrogate the size standard, interrogate or excite the fluorescent counting standard, and interrogate or excite the at least two dyes, and
   d) collecting data from at least one light scatter parameter and at least one fluorescence parameter, wherein the data collected from the at least one light scatter parameter represents a particle size based upon the size standard calibration, and wherein the data collected from the at least one parameter includes a first parameter representing presence of a non-proteinaceous material based upon intensity emitted of the first dye, a second parameter representing a particle number based upon fluorescence intensity emitted from the fluorescent counting standard, and a third parameter representing presence of a non-proteinaceous material having the physical property based upon intensity emitted from the second dye; and
   e) analyzing the data to define the particle size, the particle number, presence of the non-proteinaceous material, and presence of the physical property in order to determine an absolute number and size of non-proteinaceous subvisible particles with and without the physical property, thereby characterizing the population of subvisible particles in the sample.

2. The method of claim 1, wherein the data analysis step e) further comprises determining an absolute number of sized proteinaceous subvisible particles by subtracting an absolute number of all sized subvisible particles by the absolute number of sized non-proteinaceous subvisible particles.

3. The method of claim 1, wherein at least one of the first or second dye is a fluorescent dye.

4. The method of claim 1, wherein the interrogating step c) is performed simultaneous.

5. A method of characterizing a population of subvisible particles in a sample, the method comprising the steps of:
   a) calibrating a particle analyzer using a size standard;
   b) interrogating the sample as the sample passes through a sensing zone of the particle analyzer, the sample comprising at least one fluorescent dye,
       wherein the interrogation includes one or more wavelengths that can interrogate the size standard, and excite the at least one fluorescent dye, and
       wherein the at least one fluorescent dye includes a first fluorescent dye that stains a non-proteinaceous material in a manner that distinguishes the non-proteinaceous material from a proteinaceous material;
   c) collecting data from at least one light scatter parameter and at least one fluorescence parameter, wherein the data collected from the at least one light scatter parameter represents a particle size based upon the size standard calibration, and wherein the data collected from the at least one fluorescence parameter includes a first fluorescence parameter representing presence of the non-proteinaceous material based upon fluorescence intensity emitted from the first fluorescent dye; and
   d) analyzing the data to define the particle size and presence of the non-proteinaceous material in order to determine a size and presence of non-proteinaceous subvisible particles, thereby characterizing the population of subvisible particles in the sample.

6. The method of claim 5, wherein the size standard comprises particles having mean diameters of 0.5 µm, 1.0 µm, 2.0 µm, 4.5 µm, 6.0 µm, 10 µm, or a combination thereof.

7. The method of claim 5, wherein the first fluorescent dye has a peak fluorescence excitation wavelength from between about 300 nm to about 635 nm.

8. The method of claim 5, wherein the first fluorescent dye has a peak fluorescence emission wavelength from between about 350 nm to about 800 nm.

9. The method of claim 5, wherein
   in the interrogating the sample step b):
       the sample further comprises a fluorescent counting standard, and the interrogation includes one or more wavelengths that can interrogate or excite the fluorescent counting standard; and
   in the collection data step c):
       the at least one fluorescence parameter includes a second fluorescence parameter representing a particle number based upon fluorescence intensity emitted from the fluorescent counting standard; and
   in the data analysis step d):
       analyzing the data to define the particle number in order to determine an absolute number of the sized non-proteinaceous subvisible particles, thereby characterizing the population of subvisible particles in the sample.

10. The method of claim 9, wherein the fluorescent counting standard comprises particles having a peak fluorescence excitation wavelength from between about 300 nm to about 635 nm.

11. The method of claim 9, wherein the fluorescent counting standard comprises particles having a peak fluorescence emission wavelength from between about 385 nm and about 800 nm.

12. The method of claim 9, wherein the data analysis step d) further comprises determining absolute number of sized proteinaceous subvisible particles by subtracting the absolute number of all sized subvisible particles by the absolute number of sized non-proteinaceous subvisible particles.

13. The method of claim 9, wherein
   in the interrogating the sample step b):
       the at least one fluorescent dye further includes a second fluorescent dye that stains a physical property of the non-proteinaceous material in a manner that distinguishes a non-proteinaceous material having the physical property from a non-proteinaceous material not having the physical property, and the interrogation includes one or more wavelengths that can excite the second fluorescent dye; and
   in the collection data step c):
       collecting data further includes collecting data from a third fluorescence parameter, the third fluorescence parameter representing presence of the non-proteinaceous material having the physical property based upon fluorescence intensity emitted from the second fluorescent dye; and in the data analysis step d):

further comprises analyzing the data to define presence of the physical property in order to determine a fraction of counted, sized non-proteinaceous subvisible particles with or without the physical property, thereby characterizing the population of subvisible particles in the sample.

14. The method of claim 13, wherein the physical property is a structural feature or chemical modification.

15. The method of claim 13, wherein the second fluorescent dye has a peak fluorescence excitation wavelength from between about 350 nm to about 635 nm.

16. The method of claim 13, wherein the second fluorescent dye has a peak fluorescence emission wavelength from between about 350 nm to about 800 nm.

17. The method of claim 5, wherein the sample is a pharmaceutical preparation.

18. The method of claim 17, wherein the pharmaceutical preparation comprises a non-proteinaceous material that is a pharmaceutical active ingredient, an adjuvant, or an excipient.

19. The method of claim 5, wherein the particle size based upon the size standard calibration comprising sizes less than or equal to 10 μm, less than or equal to 20 μm, less than or equal to 50 μm, less than or equal to 75 μm, less than or equal to 100 μm, less than or equal to 200 μm, or less than or equal to 300 μm.

* * * * *